(12) United States Patent
Abbasi et al.

(10) Patent No.: US 12,214,501 B2
(45) Date of Patent: Feb. 4, 2025

(54) ROBOTIC SURGICAL SYSTEM WITH RECOVERY ALIGNMENT

(71) Applicant: MAKO Surgical Corp., Weston, FL (US)

(72) Inventors: Abdullah Abbasi, San Diego, CA (US); Amar Bhatt, Syracuse, NY (US); Andrei Danilchenko, Miami, FL (US)

(73) Assignee: MAKO Surgical Corp., Weston, FL (US)

( * ) Notice: Subject to any disclaimer, the term of this patent is extended or adjusted under 35 U.S.C. 154(b) by 625 days.

(21) Appl. No.: 17/513,368

(22) Filed: Oct. 28, 2021

(65) Prior Publication Data

US 2022/0133419 A1 May 5, 2022

Related U.S. Application Data

(60) Provisional application No. 63/189,508, filed on May 17, 2021, provisional application No. 63/131,654, (Continued)

(51) Int. Cl.
  *B25J 9/16* (2006.01)
  *A61B 17/14* (2006.01)
  (Continued)

(52) U.S. Cl.
  CPC .......... *B25J 9/1664* (2013.01); *A61B 17/142* (2016.11); *A61B 34/20* (2016.02); *A61B 34/25* (2016.02);
  (Continued)

(58) Field of Classification Search
  CPC ...... B25J 9/1664; B25J 9/1689; B25J 9/1692; A61B 17/142; A61B 34/20; A61B 34/25; A61B 34/30; A61B 34/32; A61B 2034/2055; A61B 2034/2059; A61B 2034/252; A61B 2034/107;
  (Continued)

(56) References Cited

U.S. PATENT DOCUMENTS 4,559,936 A   12/1985  Hill
5,078,140 A   1/1992   Kwoh
(Continued)

FOREIGN PATENT DOCUMENTS

EP   1 518 501 A2   3/2005
EP   1 690 503 A1   8/2006
(Continued)

OTHER PUBLICATIONS

US 9,445,923 B2, 09/2016, Arthromeda (withdrawn)
(Continued)

*Primary Examiner* — Jason Holloway
*Assistant Examiner* — Madison B Emmett
(74) *Attorney, Agent, or Firm* — FOLEY & LARDNER LLP

(57) ABSTRACT

A method of operation of a robotically-assisted surgical system includes defining a virtual geometry associated with a planned resection, determining a first pose of a surgical tool, defining a target orientation for the surgical tool based on the first pose, controlling a robotic device to automatically move the surgical tool to both the virtual geometry and the target orientation

19 Claims, 14 Drawing Sheets

Related U.S. Application Data filed on Dec. 29, 2020, provisional application No. 63/125,481, filed on Dec. 15, 2020, provisional application No. 63/107,781, filed on Oct. 30, 2020.

(51) Int. Cl.
*A61B 34/00* (2016.01)
*A61B 34/20* (2016.01)
*A61B 34/30* (2016.01)
*A61B 34/32* (2016.01)
*G05B 15/02* (2006.01)
*G16H 20/40* (2018.01)
*G16H 40/67* (2018.01)

(52) U.S. Cl.
CPC .............. *A61B 34/30* (2016.02); *A61B 34/32* (2016.02); *B25J 9/1689* (2013.01); *B25J 9/1692* (2013.01); *G05B 15/02* (2013.01); *G16H 20/40* (2018.01); *G16H 40/67* (2018.01); *A61B 2034/2055* (2016.02); *A61B 2034/2059* (2016.02); *A61B 2034/252* (2016.02)

(58) Field of Classification Search
CPC ...... A61B 2034/108; A61B 2034/2068; G05B 15/02; G16H 20/40; G16H 40/67
See application file for complete search history.

(56) References Cited

U.S. PATENT DOCUMENTS

| | | |
|---|---|---|
| 5,413,573 A | 5/1995 | Koivukangas |
| 5,540,696 A | 7/1996 | Booth et al. |
| 5,630,431 A | 5/1997 | Taylor |
| 5,682,886 A | 11/1997 | Delp et al. |
| 5,800,438 A | 9/1998 | Tuke et al. |
| 5,824,085 A | 10/1998 | Sahay et al. |
| 6,328,752 B1 | 12/2001 | Sjostrom et al. |
| 6,595,997 B2 | 7/2003 | Axelson et al. |
| 6,685,711 B2 | 2/2004 | Axelson et al. |
| 6,758,850 B2 | 7/2004 | Smith et al. |
| 6,827,723 B2 | 12/2004 | Carson |
| 6,859,661 B2 | 2/2005 | Tuke |
| 7,008,362 B2 | 3/2006 | Fitzgibbon |
| 7,412,897 B2 | 8/2008 | Crottet et al. |
| 7,510,557 B1 | 3/2009 | Bonutti |
| 7,547,307 B2 | 6/2009 | Carson et al. |
| 7,591,821 B2 | 9/2009 | Kelman |
| 7,607,440 B2 | 10/2009 | Coste-Maniere et al. |
| 7,618,421 B2 | 11/2009 | Axelson et al. |
| 7,634,306 B2 | 12/2009 | Sarin et al. |
| 7,670,345 B2 | 3/2010 | Plassky et al. |
| 7,696,899 B2 | 4/2010 | Immerz et al. |
| 7,794,467 B2 | 9/2010 | McGinley et al. |
| 7,809,421 B1 | 10/2010 | Govari |
| 7,831,295 B2 | 11/2010 | Friedrich et al. |
| 7,927,336 B2 | 4/2011 | Rasmussen |
| 7,931,655 B2 | 4/2011 | Axelson et al. |
| 7,945,310 B2 | 5/2011 | Gattani et al. |
| 7,963,913 B2 | 6/2011 | Devengenzo et al. |
| 8,007,448 B2 | 8/2011 | Moctezuma De La Barrera |
| 8,010,180 B2 | 8/2011 | Quaid et al. |
| 8,038,683 B2 | 10/2011 | Couture et al. |
| 8,075,317 B2 | 12/2011 | Youngblood |
| 8,078,440 B2 | 12/2011 | Otto et al. |
| 8,096,997 B2 | 1/2012 | Plaskos et al. |
| 8,109,942 B2 | 2/2012 | Carson |
| 8,116,847 B2 | 2/2012 | Gattani et al. |
| 8,126,533 B2 | 2/2012 | Lavallee |
| 8,160,345 B2 | 4/2012 | Pavlovskaia et al. |
| 8,170,888 B2 | 5/2012 | Silverman |
| 8,172,775 B2 | 5/2012 | Warkentine et al. |
| 8,197,549 B2 | 6/2012 | Amirouche et al. |
| 8,257,360 B2 | 9/2012 | Richard et al. |
| 8,265,790 B2 | 9/2012 | Amiot et al. |
| 8,265,949 B2 | 9/2012 | Haddad |
| 8,277,455 B2 | 10/2012 | Couture et al. |
| 8,337,508 B2 | 12/2012 | Lavallee et al. |
| 8,357,111 B2 | 1/2013 | Caillouette et al. |
| 8,377,129 B2 | 2/2013 | Fitz et al. |
| 8,382,765 B2 | 2/2013 | Axelson et al. |
| 8,386,077 B2 | 2/2013 | Birkenbach et al. |
| 8,480,679 B2 | 7/2013 | Park et al. |
| 8,483,469 B2 | 7/2013 | Pavlovskaia et al. |
| 8,521,252 B2 | 8/2013 | Diez |
| 8,545,509 B2 | 10/2013 | Park et al. |
| 8,548,559 B2 | 10/2013 | Hodgson et al. |
| 8,551,023 B2 | 10/2013 | Sherman et al. |
| 8,551,099 B2 | 10/2013 | Lang et al. |
| 8,626,267 B2 | 1/2014 | Lavallee |
| 8,641,726 B2 | 2/2014 | Bonutti |
| 8,682,052 B2 | 3/2014 | Fitz et al. |
| 8,707,963 B2 | 4/2014 | Davis et al. |
| 8,715,291 B2 | 5/2014 | Park et al. |
| 8,721,568 B2 | 5/2014 | Rock et al. |
| 8,777,875 B2 | 7/2014 | Park |
| 8,801,719 B2 | 8/2014 | Park et al. |
| 8,801,720 B2 | 8/2014 | Park et al. |
| 8,832,019 B2 | 9/2014 | Gao |
| 8,834,490 B2 | 9/2014 | Bonutti |
| 8,845,645 B2 | 9/2014 | Wilkinson et al. |
| 8,861,818 B2 | 10/2014 | Ito et al. |
| 8,880,152 B2 | 11/2014 | Lavallee |
| 8,885,904 B2 | 11/2014 | Darrow et al. |
| 8,938,282 B2 | 1/2015 | Daon et al. |
| 8,951,260 B2 | 2/2015 | Lang et al. |
| 8,956,355 B2 | 2/2015 | Edwards et al. |
| 8,965,483 B2 | 2/2015 | Couture et al. |
| 8,974,468 B2 | 3/2015 | Borja |
| 8,979,859 B2 | 3/2015 | Leparmentier et al. |
| 9,002,426 B2 | 4/2015 | Quaid et al. |
| 9,101,394 B2 | 8/2015 | Arata et al. |
| 9,119,722 B1 | 9/2015 | Kusuma |
| 9,125,669 B2 | 9/2015 | Ranawat et al. |
| 9,167,989 B2 | 10/2015 | Odermatt et al. |
| 9,168,153 B2 | 10/2015 | Bettenga |
| 9,173,716 B2 | 11/2015 | Kasodekar et al. |
| 9,186,292 B2 | 11/2015 | Besendorfer |
| 9,220,510 B2 | 12/2015 | Cheal et al. |
| 9,237,951 B1 | 1/2016 | Hakki |
| 9,241,801 B1 | 1/2016 | Parry et al. |
| 9,247,998 B2 | 2/2016 | Hladio et al. |
| 9,248,001 B2 | 2/2016 | Colombet et al. |
| 9,259,290 B2 | 2/2016 | Jenkins et al. |
| 9,262,802 B2 | 2/2016 | Aghazadeh |
| 9,265,447 B2 | 2/2016 | Stein et al. |
| 9,271,756 B2 | 3/2016 | Van Der Walt et al. |
| 9,277,968 B2 | 3/2016 | Min et al. |
| 9,286,355 B2 | 3/2016 | De Guise et al. |
| 9,289,264 B2 | 3/2016 | Iorgulescu et al. |
| 9,301,812 B2 | 4/2016 | Kehres et al. |
| 9,332,987 B2 | 5/2016 | Leimbach et al. |
| 9,406,134 B2 | 8/2016 | Klingenbeck-Regn |
| 9,433,425 B2 | 9/2016 | Wilkinson |
| 9,439,656 B2 | 9/2016 | Chana et al. |
| 9,517,000 B2 | 12/2016 | Donhowe et al. |
| 9,532,788 B2 | 1/2017 | Jordan et al. |
| 9,532,838 B2 | 1/2017 | Coste-Maniere et al. |
| 9,549,742 B2 | 1/2017 | Berend et al. |
| 9,549,782 B2 | 1/2017 | Park et al. |
| 9,554,953 B2 | 1/2017 | Dirauf et al. |
| 9,561,082 B2 | 2/2017 | Yen et al. |
| 9,572,682 B2 | 2/2017 | Aghazadeh |
| 9,585,725 B2 | 3/2017 | Bonutti |
| 9,585,768 B2 | 3/2017 | Sherman et al. |
| 9,592,133 B2 | 3/2017 | Toler et al. |
| 9,597,096 B2 | 3/2017 | Aghazadeh |
| 9,610,086 B2 | 4/2017 | Park et al. |
| 9,610,134 B2 | 4/2017 | Kubiak et al. |
| 9,639,156 B2 | 5/2017 | Iorgulescu et al. |
| 9,684,768 B2 | 6/2017 | Lavallee et al. |
| 9,700,292 B2 | 7/2017 | Nawana et al. |
| 9,724,165 B2 | 8/2017 | Arata et al. |

(56) References Cited

U.S. PATENT DOCUMENTS

| | | |
|---|---|---|
| 9,737,311 B2 | 8/2017 | Lavallee et al. |
| 9,737,369 B2 | 8/2017 | Burger et al. |
| 9,763,683 B2 | 9/2017 | Bonutti |
| 9,763,746 B2 | 9/2017 | Deichmann et al. |
| 9,782,226 B2 | 10/2017 | Park et al. |
| 9,782,229 B2 | 10/2017 | Crawford et al. |
| 9,808,356 B2 | 11/2017 | Haight et al. |
| 9,848,896 B2 | 12/2017 | Emslie et al. |
| 9,861,446 B2 | 1/2018 | Lang |
| 9,888,931 B2 | 2/2018 | Bake |
| 9,901,404 B2 | 2/2018 | Park et al. |
| 9,901,463 B2 | 2/2018 | Mahfouz |
| 9,911,187 B2 | 3/2018 | Steinle et al. |
| 9,913,691 B2 | 3/2018 | Brooks |
| 9,913,692 B2 | 3/2018 | Arata et al. |
| 9,916,421 B2 | 3/2018 | Vorhis et al. |
| 9,987,092 B2 | 6/2018 | Hladio et al. |
| 10,010,377 B2 | 7/2018 | Iorgulescu et al. |
| 10,052,164 B2 | 8/2018 | Overmyer |
| 10,070,931 B2 | 9/2018 | Itkowitz et al. |
| 10,070,973 B2 | 9/2018 | Sherman et al. |
| 10,071,488 B2 | 9/2018 | Robinson et al. |
| 10,076,344 B2 | 9/2018 | Toler |
| 10,080,616 B2 | 9/2018 | Wilkinson et al. |
| 10,092,361 B2 | 10/2018 | Ferro et al. |
| 10,102,309 B2 | 10/2018 | McKinnon et al. |
| 10,117,658 B2 | 11/2018 | Talbot |
| 10,130,375 B2 | 11/2018 | Yager et al. |
| 10,136,950 B2 | 11/2018 | Schoenefeld |
| 10,136,952 B2 | 11/2018 | Couture et al. |
| 10,172,687 B2 | 1/2019 | Garbus et al. |
| 10,194,991 B2 | 2/2019 | Bonny et al. |
| 10,201,320 B2 | 2/2019 | Saget et al. |
| 10,206,714 B2 | 2/2019 | Van Der Walt et al. |
| 10,206,792 B2 | 2/2019 | Sherman et al. |
| 10,226,261 B2 | 3/2019 | Park et al. |
| 10,226,306 B2 | 3/2019 | Itkowitz et al. |
| 10,231,739 B1 | 3/2019 | Bonutti |
| 10,231,786 B2 | 3/2019 | Ferro et al. |
| 10,238,454 B2 | 3/2019 | Boettner et al. |
| 10,271,954 B2 | 4/2019 | Roach et al. |
| 10,272,569 B2 | 4/2019 | Swarup et al. |
| 10,278,777 B1 | 5/2019 | Lang |
| 10,285,683 B2 | 5/2019 | Plaskos et al. |
| 10,307,269 B2 | 6/2019 | Miller |
| 10,368,947 B2 | 8/2019 | Lang |
| 10,416,624 B2 | 9/2019 | Bly et al. |
| 10,420,611 B2 | 9/2019 | Jaramaz et al. |
| 10,426,556 B2 | 10/2019 | Miga et al. |
| 10,441,366 B2 | 10/2019 | Tabandeh et al. |
| 10,441,438 B1 | 10/2019 | Rahman et al. |
| 10,452,238 B2 | 10/2019 | Nikou et al. |
| 10,456,075 B2 | 10/2019 | Auchinleck et al. |
| 10,456,166 B2 | 10/2019 | Cooper et al. |
| 10,463,242 B2 | 11/2019 | Kesten et al. |
| 10,470,838 B2 | 11/2019 | Epstein et al. |
| 10,492,693 B2 | 12/2019 | Irisawa |
| 10,492,798 B2 | 12/2019 | Metzger |
| 10,548,667 B2 | 2/2020 | Flett et al. |
| 10,555,777 B2 | 2/2020 | Griffiths et al. |
| 10,572,733 B2 | 2/2020 | Wells et al. |
| 10,575,910 B2 | 3/2020 | Itkowitz et al. |
| 10,595,880 B2 | 3/2020 | Otto et al. |
| 10,595,887 B2 | 3/2020 | Shelton et al. |
| 10,595,952 B2 | 3/2020 | Forrest et al. |
| 10,610,310 B2 | 4/2020 | Todd et al. |
| 10,610,315 B2 | 4/2020 | Itkowitz et al. |
| 10,610,316 B2 | 4/2020 | Swarup et al. |
| 10,617,479 B2 | 4/2020 | Itkowitz et al. |
| 10,624,807 B2 | 4/2020 | Itkowitz et al. |
| 10,638,970 B2 | 5/2020 | Obma et al. |
| 10,739,963 B2 | 8/2020 | Nikou et al. |
| 10,765,384 B2 | 9/2020 | Wollowick et al. |
| 11,553,969 B1 * | 1/2023 | Lang ............... G06T 7/0012 |
| 2002/0055918 A1 | 5/2002 | Hlathein et al. |
| 2002/0082612 A1 | 6/2002 | Moll et al. |
| 2004/0260301 A1 | 12/2004 | Lionberger et al. |
| 2005/0020941 A1 | 1/2005 | Tarabichi |
| 2005/0113846 A1 | 5/2005 | Carson |
| 2005/0119661 A1 | 6/2005 | Hodgson et al. |
| 2005/0149040 A1 | 7/2005 | Haines et al. |
| 2005/0171545 A1 | 8/2005 | Walsh et al. |
| 2005/0234466 A1 | 10/2005 | Stallings |
| 2005/0251148 A1 | 11/2005 | Friedrich et al. |
| 2006/0015120 A1 | 1/2006 | Richard et al. |
| 2006/0064043 A1 | 3/2006 | Goeggelmann et al. |
| 2006/0200026 A1 | 9/2006 | Wallace et al. |
| 2006/0241405 A1 | 10/2006 | Leitner et al. |
| 2007/0073136 A1 | 3/2007 | Metzger |
| 2007/0123896 A1 | 5/2007 | Wyss et al. |
| 2007/0179626 A1 | 8/2007 | De La Barrera et al. |
| 2008/0004633 A1 | 1/2008 | Arata et al. |
| 2008/0208081 A1 | 8/2008 | Murphy et al. |
| 2008/0249394 A1 | 10/2008 | Giori et al. |
| 2008/0281301 A1 | 11/2008 | Deboer et al. |
| 2008/0281328 A1 | 11/2008 | Lang et al. |
| 2008/0281426 A1 | 11/2008 | Fitz et al. |
| 2010/0063508 A1 | 3/2010 | Borja et al. |
| 2010/0064216 A1 | 3/2010 | Borja et al. |
| 2010/0145344 A1 | 6/2010 | Jordan et al. |
| 2011/0029091 A1 | 2/2011 | Bojarski et al. |
| 2011/0071528 A1 | 3/2011 | Carson |
| 2011/0071530 A1 | 3/2011 | Carson |
| 2011/0304332 A1 | 12/2011 | Mahfouz |
| 2011/0306986 A1 | 12/2011 | Lee et al. |
| 2012/0143084 A1 | 6/2012 | Shoham |
| 2012/0226198 A1 | 9/2012 | Carson |
| 2012/0226481 A1 | 9/2012 | Carson |
| 2012/0283747 A1 * | 11/2012 | Popovic ............. A61B 34/30 606/130 |
| 2013/0072821 A1 | 3/2013 | Odermatt et al. |
| 2013/0085510 A1 | 4/2013 | Stefanchik et al. |
| 2013/0123983 A1 | 5/2013 | Brogaardh |
| 2013/0172905 A1 | 7/2013 | Iorgulescu et al. |
| 2013/0209953 A1 | 8/2013 | Arlinsky et al. |
| 2014/0039520 A1 | 2/2014 | Haider et al. |
| 2014/0073907 A1 | 3/2014 | Kumar et al. |
| 2014/0108983 A1 | 4/2014 | William R et al. |
| 2014/0128727 A1 | 5/2014 | Daon et al. |
| 2014/0135791 A1 | 5/2014 | Nikou et al. |
| 2014/0188240 A1 | 7/2014 | Lang et al. |
| 2014/0189508 A1 | 7/2014 | Granchi et al. |
| 2014/0296871 A1 | 10/2014 | Chen et al. |
| 2015/0094736 A1 | 4/2015 | Malackowski et al. |
| 2015/0105782 A1 | 4/2015 | D'Lima et al. |
| 2015/0106024 A1 | 4/2015 | Lightcap et al. |
| 2016/0007836 A1 | 1/2016 | Kikuchi |
| 2016/0022374 A1 | 1/2016 | Haider et al. |
| 2016/0220175 A1 | 8/2016 | Tam et al. |
| 2016/0278868 A1 | 9/2016 | Berend et al. |
| 2016/0338777 A1 | 11/2016 | Penenberg et al. |
| 2017/0014169 A1 | 1/2017 | Dean et al. |
| 2017/0042557 A1 | 2/2017 | Plaskos et al. |
| 2017/0061375 A1 | 3/2017 | Laster et al. |
| 2017/0196571 A1 | 7/2017 | Berend et al. |
| 2017/0252112 A1 | 9/2017 | Crawford et al. |
| 2017/0258532 A1 | 9/2017 | Shalayev et al. |
| 2017/0312099 A1 | 11/2017 | Paszicsnyek |
| 2017/0325973 A1 | 11/2017 | Bonny et al. |
| 2017/0340389 A1 | 11/2017 | Otto et al. |
| 2017/0347922 A1 | 12/2017 | Bhandari |
| 2017/0348008 A1 | 12/2017 | Lavallee et al. |
| 2018/0064496 A1 | 3/2018 | Hladio et al. |
| 2018/0071049 A1 | 3/2018 | Nowatschin et al. |
| 2018/0085135 A1 | 3/2018 | Singh et al. |
| 2018/0085172 A1 | 3/2018 | Bell et al. |
| 2018/0116739 A1 | 5/2018 | Gogarty et al. |
| 2018/0116805 A1 | 5/2018 | Johannaber et al. |
| 2018/0116823 A1 | 5/2018 | Johannaber et al. |
| 2018/0132949 A1 | 5/2018 | Merette et al. |
| 2018/0168750 A1 | 6/2018 | Staunton et al. |
| 2018/0168762 A1 | 6/2018 | Scheib et al. |
| 2018/0177512 A1 | 6/2018 | Hogan et al. |
| 2018/0185100 A1 | 7/2018 | Weinstein et al. |

(56) References Cited

U.S. PATENT DOCUMENTS

| | | |
|---|---|---|
| 2018/0199995 A1 | 7/2018 | Odermatt et al. |
| 2018/0214180 A1 | 8/2018 | Theodore et al. |
| 2018/0250078 A1 | 9/2018 | Shochat et al. |
| 2018/0256256 A1 | 9/2018 | May et al. |
| 2018/0271607 A1* | 9/2018 | Kralicky ............... B25J 11/008 |
| 2018/0317898 A1 | 11/2018 | Plaskos et al. |
| 2018/0338796 A1 | 11/2018 | Yao et al. |
| 2018/0344409 A1 | 12/2018 | Bonny et al. |
| 2018/0368930 A1 | 12/2018 | Esterberg et al. |
| 2019/0000631 A1 | 1/2019 | Blankevoort et al. |
| 2019/0008599 A1 | 1/2019 | Lynch et al. |
| 2019/0046278 A1* | 2/2019 | Steinle ................... A61B 34/30 |
| 2019/0066832 A1 | 2/2019 | Kang et al. |
| 2019/0069962 A1 | 3/2019 | Tabandeh et al. |
| 2019/0069963 A1 | 3/2019 | Azizian et al. |
| 2019/0083191 A1 | 3/2019 | Gilhooley et al. |
| 2019/0090952 A1 | 3/2019 | Bonny et al. |
| 2019/0090962 A1 | 3/2019 | Boettner |
| 2019/0099228 A1 | 4/2019 | Keller et al. |
| 2019/0117156 A1 | 4/2019 | Howard et al. |
| 2019/0117407 A1 | 4/2019 | Yang |
| 2019/0122330 A1 | 4/2019 | Saget et al. |
| 2019/0133695 A1 | 5/2019 | Hladio et al. |
| 2019/0147128 A1 | 5/2019 | O'Connor |
| 2019/0175283 A1 | 6/2019 | Bonny et al. |
| 2019/0176334 A1 | 6/2019 | Zhou et al. |
| 2019/0200900 A1 | 7/2019 | Thelen et al. |
| 2019/0201101 A1 | 7/2019 | Hafez |
| 2019/0201214 A1 | 7/2019 | Miller et al. |
| 2019/0209079 A1 | 7/2019 | Delport |
| 2019/0216520 A1 | 7/2019 | Babak et al. |
| 2019/0223962 A1* | 7/2019 | Roldan .................. A61B 34/30 |
| 2019/0224016 A1 | 7/2019 | Walker et al. |
| 2019/0240045 A1 | 8/2019 | Couture |
| 2019/0240046 A1 | 8/2019 | Couture |
| 2019/0254756 A1 | 8/2019 | Zhang et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274762 A1 | 9/2019 | Kim et al. |
| 2019/0290198 A1 | 9/2019 | Belson et al. |
| 2019/0311542 A1 | 10/2019 | Douglas et al. |
| 2019/0325386 A1 | 10/2019 | Laster et al. |
| 2019/0336220 A1 | 11/2019 | Hladio et al. |
| 2019/0365481 A1 | 12/2019 | Otto et al. |
| 2019/0374130 A1 | 12/2019 | Bydlon et al. |
| 2019/0380792 A1 | 12/2019 | Poltaretskyi et al. |
| 2019/0388153 A1 | 12/2019 | Running et al. |
| 2019/0388157 A1 | 12/2019 | Shameli et al. |
| 2020/0000400 A1 | 1/2020 | McKinnon et al. |
| 2020/0015598 A1 | 1/2020 | Hondori et al. |
| 2020/0030036 A1 | 1/2020 | Forstein |
| 2020/0060772 A1 | 2/2020 | Konh et al. |
| 2020/0060773 A1 | 2/2020 | Barral et al. |
| 2020/0100848 A1 | 4/2020 | Zuhars et al. |
| 2020/0113583 A1 | 4/2020 | Philipp et al. |
| 2020/0129311 A1 | 4/2020 | Singh et al. |
| 2020/0305978 A1 | 10/2020 | Tan et al. |
| 2020/0305979 A1 | 10/2020 | Crawford et al. |
| 2020/0323540 A1 | 10/2020 | Kang et al. |
| 2020/0352529 A1 | 11/2020 | Wollowick et al. |
| 2021/0068845 A1 | 3/2021 | Schers et al. |
| 2021/0361298 A1* | 11/2021 | Patel .................. A61B 17/1757 |
| 2022/0031398 A1* | 2/2022 | Zheng .................. A61B 34/37 |
| 2022/0071720 A1 | 3/2022 | Sexson et al. |
| 2022/0148739 A1* | 5/2022 | Farley ................... G16H 50/70 |
| 2022/0361972 A1 | 11/2022 | Armand et al. |
| 2022/0395340 A1* | 12/2022 | Dumpe .................. A61B 90/96 |
| 2023/0146679 A1* | 5/2023 | Lavallée ................. A61B 6/06 |
| | | 700/259 |

FOREIGN PATENT DOCUMENTS

| | | |
|---|---|---|
| EP | 1 226 788 B1 | 10/2006 |
| EP | 1 755 466 B1 | 12/2007 |
| EP | 2 007 291 A2 | 12/2008 |
| EP | 2 156 794 A1 | 2/2010 |
| EP | 2 384 714 A1 | 11/2011 |
| EP | 1 919 390 B1 | 12/2012 |
| EP | 1 841 372 B1 | 9/2017 |
| EP | 3 510 927 A1 | 7/2019 |
| EP | 3 334 383 B1 | 4/2020 |
| WO | WO-95/31148 A1 | 11/1995 |
| WO | WO-2004/070580 A2 | 8/2004 |
| WO | WO-2006/078236 A1 | 7/2006 |
| WO | WO-2007/092841 A1 | 8/2007 |
| WO | WO-2012/082164 A1 | 6/2012 |
| WO | WO-2012/101286 A1 | 8/2012 |
| WO | WO-2015/057814 A1 | 4/2015 |
| WO | WO-2016/146768 A1 | 9/2016 |
| WO | WO-2016/198844 A1 | 12/2016 |
| WO | WO-2017/076886 A1 | 5/2017 |
| WO | WO-2017/108776 A1 | 6/2017 |
| WO | WO-2017/115235 A1 | 7/2017 |
| WO | WO-2017/124043 A1 | 7/2017 |
| WO | WO-2017/147596 A1 | 8/2017 |
| WO | WO-2017/179075 A1 | 10/2017 |
| WO | WO-2018/085694 A1 | 5/2018 |
| WO | WO-2018/085900 A1 | 5/2018 |
| WO | WO-2018/095499 A1 | 5/2018 |
| WO | WO-2018/104704 A1 | 6/2018 |
| WO | WO-2018/161120 A1 | 9/2018 |
| WO | WO-2019/006370 A1 | 1/2019 |
| WO | WO-2019/032828 A2 | 2/2019 |
| WO | WO-2019/068194 A1 | 4/2019 |
| WO | WO-2019/079634 A1 | 4/2019 |
| WO | WO-2019/081915 A1 | 5/2019 |
| WO | WO-2019/135805 A1 | 7/2019 |
| WO | WO-2019/148154 A1 | 8/2019 |
| WO | WO-2019/191722 A1 | 10/2019 |
| WO | WO-2019/224745 A1 | 11/2019 |
| WO | WO-2019/241516 A1 | 12/2019 |
| WO | WO-2019/245849 A1 | 12/2019 |
| WO | WO-2019/245851 A1 | 12/2019 |
| WO | WO-2020/033568 A2 | 2/2020 |
| WO | WO-2020/056443 A1 | 3/2020 |
| WO | WO-2020/065209 A1 | 4/2020 |
| WO | WO-2020/227832 A1 | 11/2020 |

OTHER PUBLICATIONS

International Search Report and Written Opinion for International Application No. PCT/US2021/057024, mailed Feb. 16, 2022, 17 pages.

International Search Report and Written Opinion for International Application No. PCT/US2021/057045, mailed Feb. 14, 2022, 17 pages.

International Search Report and Written Opinion for International Application No. PCT/US2021/057065, mailed Feb. 18, 2022, 19 pages.

* cited by examiner

ROBOTIC SURGICAL SYSTEM WITH RECOVERY ALIGNMENT

CROSS-REFERENCE TO RELATED APPLICATIONS

This application claims the benefit of and priority to U.S. Provisional Patent Application No. 63/107,781, filed Oct. 30, 2020, U.S. Provisional Patent Application No. 63/125,481 filed Dec. 15, 2020, U.S. Provisional Patent Application No. 63/131,654 filed Dec. 29, 2020, and U.S. Provisional Patent Application No. 63/189,508 filed May 17, 2021, the entire disclosures of which are incorporated by reference herein.

BACKGROUND

The present disclosure relates generally to surgical systems for orthopedic surgeries, for example surgical systems that facilitate joint replacement procedures. Joint replacement procedures (arthroplasty procedures) are widely used to treat osteoarthritis and other damage to a patient's joint by replacing portions of the joint with prosthetic components. Joint replacement procedures can include procedures to replace hips, knees, shoulders, or other joints with one or more prosthetic components.

One possible tool for use in an arthroplasty procedure is a robotically-assisted surgical system. A robotically-assisted surgical system typically includes a robotic device that is used to prepare a patient's anatomy to receive an implant, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical tool during portions of the surgical procedure. Guidance and/or control of the surgical tool serves to assist the surgeon during implementation of the surgical plan. Various features enabling improved planning, improved intra-operative assessments of the patient biomechanics, intraoperative plan adjustments, etc. for use with robotically-assisted surgical systems or other computer-assisted surgical systems may be advantageous.

SUMMARY

Figure 1:
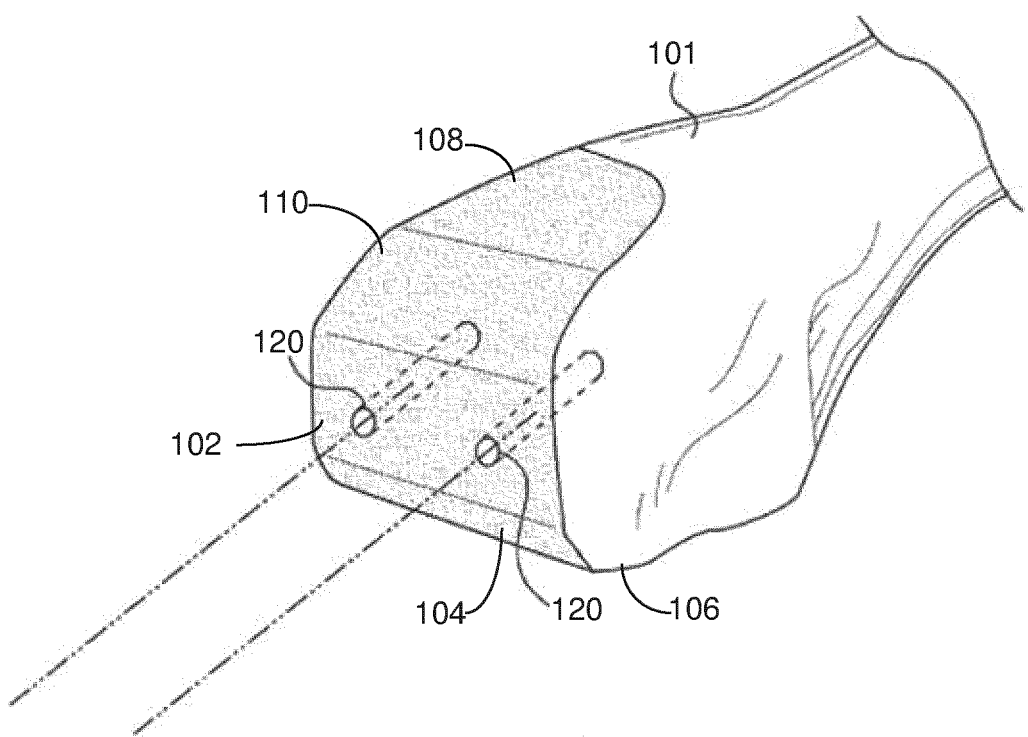
FIG. 1 is a perspective view of a femur prepared to receive an implant component, according to an exemplary embodiment.

One implementation of the present disclosure is a method of operation of a robotically-assisted surgical system. The method includes defining a virtual geometry associated with a planned resection, determining a first pose of a surgical tool, defining a target orientation for the surgical tool based on the first pose, controlling a robotic device to automatically move the surgical tool to both the virtual geometry and the target orientation.

In some embodiments, determining the first pose of the surgical tool includes detecting an interruption of performance of the planned resection and determining the first pose based on an angle of the surgical tool in the virtual geometry at the interruption. Defining the target orientation for the surgical tool based on the first pose can include defining the target orientation to match the angle of the surgical tool in the virtual geometry at the interruption. Controlling the robotic device to automatically move the surgical tool into both the virtual geometry and the target orientation may cause the surgical tool to return to the angle of the surgical tool in the virtual geometry at the interruption In some embodiments, determining the first pose of the surgical tool includes detecting a user request to initiate automated alignment of the surgical tool to the virtual geometry and determining the first pose as a current pose of the surgical tool when the user request is detected.

In some embodiments, defining the target orientation for the surgical tool based on the first pose includes determining whether the first pose is in a first category or a second category and defining the target orientation as a first orientation if the first pose is in the first category and defining the target orientation as a second orientation if the first pose is in the second category. The first category may correspond to poses in which the surgical tool points at least partially in a medial-to-lateral direction with respect to a joint of a patient and the second category may correspond to poses in which the surgical tool points at least partially in a lateral-to-medial direction with respect to the joint of the patient. The first orientation may be dynamically defined to comprise an angle of the first pose and the second orientation may be static and predefined, for example perpendicular to the medial-to-lateral and lateral-to-medial directions of the joint.

In some embodiments, controlling the robotic device to automatically move the surgical tool to both the virtual geometry and the target orientation comprises causing the robotic device to automatically move for a duration greater than a preset lower bound on the duration and less than a preset upper bound on the duration.

Another implementation of the present disclosure is a surgical system. The surgical system includes a robotic device, a surgical tool coupled to the robotic device, and a controller. The controller is configured to define a plane for performing a cut of a bone, control the robotic device to allow manual movement of the surgical tool in the plane while the surgical tool is used to perform the cut of the bone, detect an interruption of performance of the cut, determine a last angular orientation of the surgical tool in the plane before occurrence of the interruption, and control the robotic device to automatically realign the surgical tool to both the plane and the last angular orientation of the surgical tool.

In some embodiments, the interruption is caused by a deviation from the plane. The controller is configured to determine whether the deviation exceeds a threshold. In response to determining that the deviation exceeds the threshold, the controller is configured to control the robotic device to move the surgical tool to a first distance from the bone while automatically realigning the surgical tool to both the plane and the last angular orientation of the surgical tool. In response to determining that the deviation does not exceed the threshold, the controller is configured to control the robotic device to move the surgical tool to a second distance from the bone while automatically realigning the surgical tool to both the plane and the last angular orientation of the surgical tool. The second distance may be less than the first distance. The interruption may include (e.g., be caused by) an occlusion of a tracking system or a deviation of the surgical tool from the plane.

Another implementation of the present disclosure is non-transitory computer-readable media storing program instructions that, when executed by one or more processors, cause the one or more processors to perform operations comprising defining a virtual geometry relative to an anatomical feature, controlling a robotic device coupled to a tool to guide the tool with the virtual geometry, detecting a deviation of the tool from the virtual geometry, controlling the robotic device to automatically move the tool to a first position having a first distance from the anatomical feature if the deviation exceeds a threshold, and controlling the robotic device to automatically move the tool to a second position having a second distance from the anatomical feature if the deviation is less than the threshold.

In some embodiments, the second distance is less than the first distance. The first position and the second position may be aligned with the virtual geometry.

In some embodiments the operations also include determining a last angular orientation of the tool in the virtual geometry before occurrence of the deviation. Controlling the robotic device to automatically move the tool to the second position can include automatically aligning the surgical tool to the last angular orientation of the surgical tool. Controlling the robotic device to automatically move the tool to the second position can also include automatically aligning the surgical tool to the last angular orientation of the surgical tool.

DETAILED DESCRIPTION

Presently preferred embodiments of the invention are illustrated in the drawings. An effort has been made to use the same or like reference numbers throughout the drawings to refer to the same or like parts. Although this specification refers primarily to a robotic arm for orthopedic joint replacement, it should be understood that the subject matter described herein is applicable to other types of robotic systems, including those used for non-surgical applications, as well as for procedures directed to other anatomical regions, for example spinal or dental procedures.

Referring now to FIG. 1, a femur 101 as modified during a knee arthroplasty procedure is shown, according to an exemplary embodiment. As shown in FIG. 1, the femur 101 has been modified with multiple planar cuts. In the example shown, the femur 100 has been modified by five substantially planar cuts to create five substantially planar surfaces, namely distal surface 102, posterior chamfer surface 104, posterior surface 106, anterior surface 108, and anterior chamfer surface 110. The planar surfaces may be achieved using a sagittal saw or other surgical tool, for example a surgical tool coupled to a robotic device as in the examples described below. The planar surfaces 102-110 are created such that the planar surfaces 102-110 will mate with corresponding surfaces of a femoral implant component. The positions and angular orientations of the planar surfaces 102-110 may determine the alignment and positioning of the implant component. Accordingly, operating a surgical tool to create the planar surfaces 102-110 with a high degree of accuracy may improve the outcome of a joint replacement procedure.

As shown in FIG. 1, the femur 101 has also been modified to have a pair of pilot holes 120. The pilot holes 120 extend into the femur 101 and are created such that the pilot holes 120 can receive a screw, a projection extending from a surface of an implant component, or other structure configured to facilitate coupling of an implant component to the femur 101. The pilot holes 120 may be created using a drill, spherical burr, or other surgical tool as described below. The pilot holes 120 may have a pre-planned position, orientation, and depth, which facilitates secure coupling of the implant component to the bone in a desired position and orientation. In some cases, the pilot holes 120 are planned to intersect with higher-density areas of a bone and/or to avoid other implant components and/or sensitive anatomical features. Accordingly, operating a surgical tool to create the pilot holes 120 with a high degree of accuracy may improve the outcome of a joint replacement procedure.

A tibia may also be modified during a joint replacement procedure. For example, a planar surface may be created on the tibia at the knee joint to prepare the tibia to mate with a tibial implant component. In some embodiments, one or more pilot holes or other recess (e.g., fin-shaped recess) may also be created in the tibia to facilitate secure coupling of an implant component tot eh bone.

In some embodiments, the systems and methods described herein provide robotic assistance for creating the planar surfaces 102-110 and the pilot holes 120 at the femur, and/or a planar surface and/or pilot holes 120 or other recess on a tibia. It should be understood that the creation of five planar cuts and two cylindrical pilot holes as shown in FIG.

1 is an example only, and that the systems and methods described herein may be adapted to plan and facilitate creation of any number of planar or non-planar cuts, any number of pilot holes, any combination thereof, etc., for preparation of any bone and/or joint in various embodiments. For example, in a hip or shoulder arthroplasty procedure, a spherical burr may be used in accordance with the systems and methods herein to ream a curved surface configured to receive a curved implant cup. Furthermore, in other embodiments, the systems and methods described herein may be used to facilitate placement an implant component relative to a bone (e.g., to facilitate impaction of cup implant in a hip arthroplasty procedure). Many such surgical and non-surgical implementations are within the scope of the present disclosure.

The positions and orientations of the planar surfaces 102-110, pilot holes 120, and any other surfaces or recesses created on bones of the knee joint can affect how well implant components mate to the bone as well as the resulting biomechanics for the patient after completion of the surgery. Tension on soft tissue can also be affected. Accordingly, systems and methods for planning the cuts which create these surfaces, facilitating intra-operative adjustments to the surgical plan, and providing robotic-assistance or other guidance for facilitating accurate creation of the planar surfaces 102-110, other surfaces, pilot holes 120, or other recesses can make surgical procedures easier and more efficient for healthcare providers and improve surgical outcomes.

Figure 2:
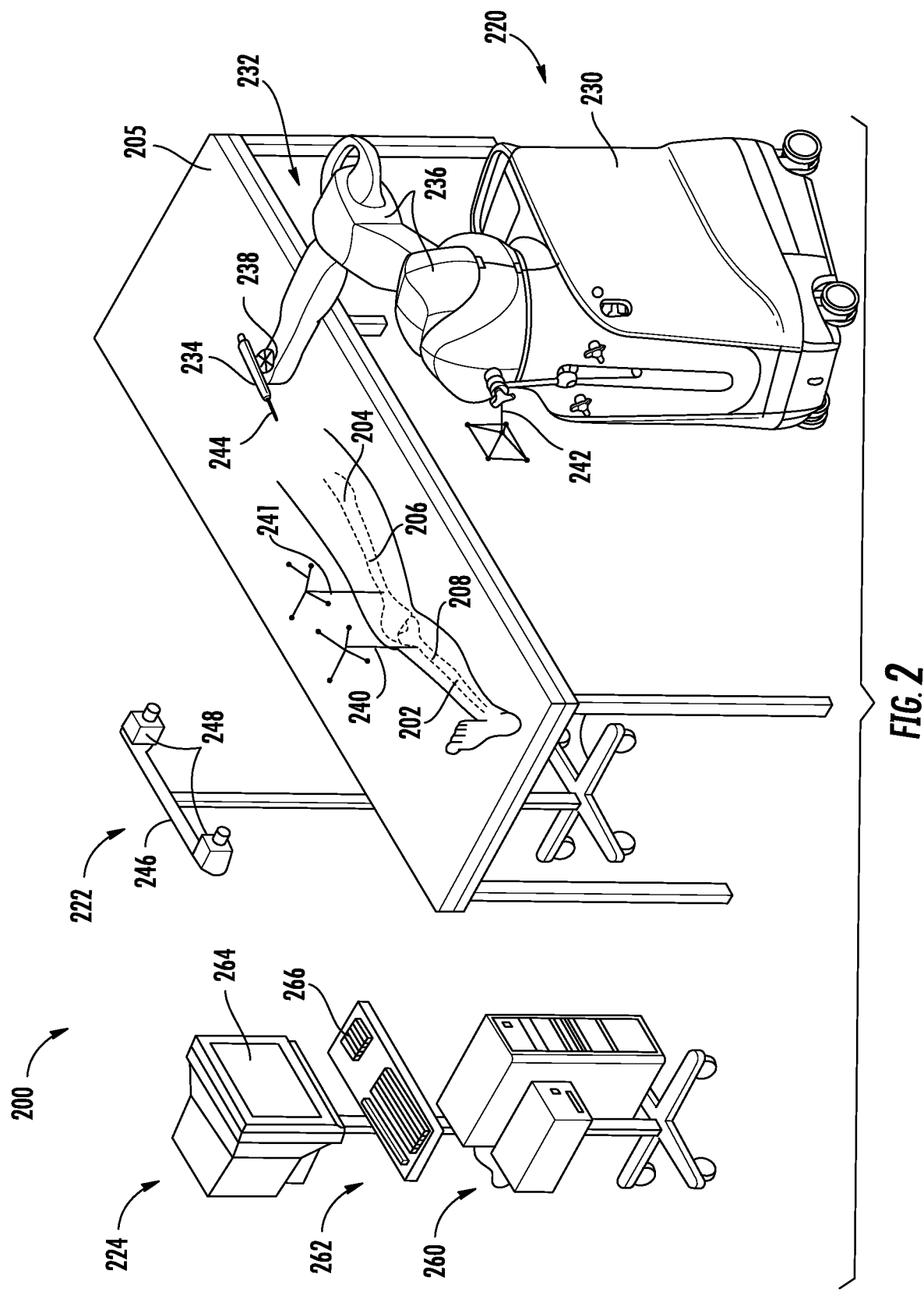
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 (e.g., femur 101 of FIG. 1) and tibia 208, between which a prosthetic knee implant is to be implanted in a total knee arthroscopy procedure. In other scenarios, the surgical system 200 is set up to treat a hip of a patient, i.e., the femur and the pelvis of the patient. Additionally, in still other scenarios, the surgical system 200 is set up to treat a shoulder of a patient, i.e., to facilitate replacement and/or augmentation of components of a shoulder joint (e.g., to facilitate placement of a humeral component, a glenoid component, and a graft or implant augment). Various other anatomical regions and procedures are also possible.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, burr, grind, drill, partially resect, reshape, and/or otherwise modify a bone. The surgical tool 234 may be any suitable tool, and may be one of multiple tools interchangeably connectable to robotic device 220. For example, as shown in FIG. 2 the surgical tool 234 includes a spherical burr 244. In other examples, the surgical tool may also be a sagittal saw, for example with a blade aligned parallel with a tool axis or perpendicular to the tool axis. The surgical tool may also be a drill, for example with a rotary bit aligned parallel with a tool axis or perpendicular to the tool axis. The surgical tool 234 may also be a holding arm or other support configured to hold an implant component (e.g., cup 28a, implant augment, etc.) in position while the implant component is screwed to a bone, adhered (e.g., cemented) to a bone or other implant component, or otherwise installed in a preferred position. In some embodiments, the surgical tool 234 is an impaction tool configured to provide an impaction force to a cup implant to facilitate fixation of the cup implant to a pelvis in a planned location and orientation.

Tracking system 222 is configured track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of modifications or other results made by the surgical tool 234, and allow a user to visualize the bones (e.g., femur 206, the tibia 208, pelvis, humerus, scapula, etc. as applicable in various procedures), the surgical tool 234, and/or the robotic arm 232 on a display of the computing system 224. The tracking system 222 can also be used to collect biomechanical measurements relating to the patient's anatomy, assess joint gap distances, identify a hip center point, assess native or corrected joint deformities, or otherwise collect information relating to the relative poses of anatomical features. More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials attachable to surgical tool 234, and a detection device 246 configured to detect the three-dimensional position of fiducials (i.e., markers on fiducial trees 240-242). Fiducial trees 240, 241 may be coupled to other bones as suitable for various procedures (e.g., pelvis and femur in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). In some embodiments, the markers are active light emitting diodes. A stereoscopic arrangement of cameras 248 on detection device 246 allows the position of each fiducial to be determined in 3D-space through a triangulation approach in the example shown. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed. The imaging data may be created using any suitable medical imaging technique to image the relevant anatomical feature, including computed tomography (CT), magnetic resonance imaging (MRI), and/or ultrasound. The imaging data is then segmented (i.e., the regions in the imaging corresponding to different anatomical features are distinguished) to obtain the virtual bone model. For example, MRI-based scan data of a joint can be segmented to distinguish bone from surrounding ligaments, cartilage, previously-implanted prosthetic components, and other tissue to obtain a three-dimensional model of the imaged bone.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, the surgical plan may be generated and/or modified based on distraction force measurements collected intraoperatively.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, the preoperative plan may include the modifications necessary to create holes (e.g., pilot holes 120) in a bone. As another example, in a hip arthroplasty procedure, the surgical plan may include the burr necessary to form one or more surfaces on the acetabular region of the pelvis to receive a cup and, in suitable cases, an implant augment. Accordingly, the processing circuit 260 may receive, access, and/or store a model of the prosthetic to facilitate the generation of surgical plans. In some embodiments, the processing circuit facilitate intraoperative modifications tot eh preoperative plant.

The processing circuit 260 is further configured to generate a control object for the robotic device 220 in accordance with the surgical plan. The control object may take various forms according to the various types of possible robotic devices (e.g., haptic, autonomous). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup implant and/or implant augment. A line haptic object may correspond to a pilot hole to be made in a bone to prepare the bone to receive a screw or other projection.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. Where one HIP is used to virtually represent a surgical tool, the HIP may be referred to herein as a tool center point (TCP). If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010,180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

Figure 3:
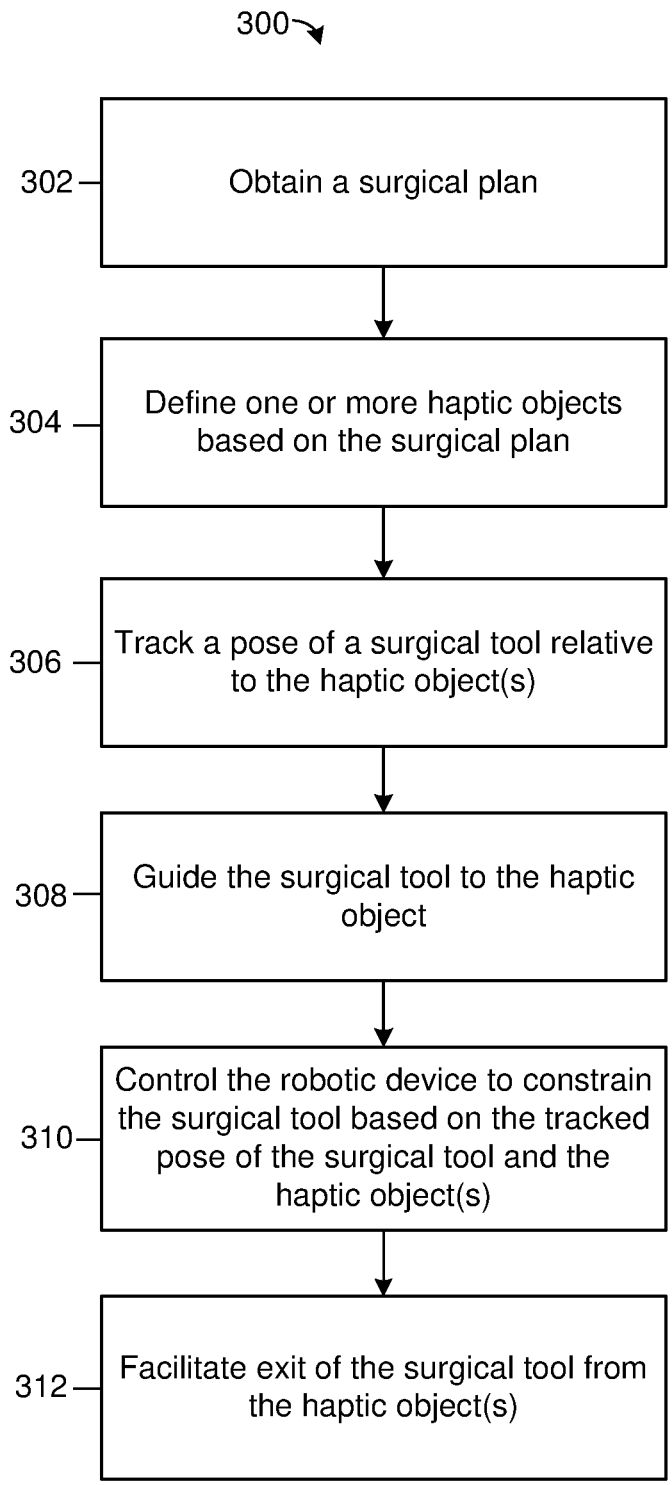
FIG. 3 is a flowchart of a first process that can be executed by the surgical system of FIG. 2, according to an exemplary embodiment.

Referring now to FIG. 3, a flowchart of a process 300 that can be executed by the surgical system 200 of FIG. 2 is shown, according to an exemplary embodiment. Process 300 may be adapted to facilitate various surgical procedures, including total and partial joint replacement surgeries.

At step 302, a surgical plan is obtained. The surgical plan (e.g., a computer-readable data file) may define a desired outcome of bone modifications, for example defined based on a desired position of prosthetic components relative to the patient's anatomy. For example, in the case of a knee arthroplasty procedure, the surgical plan may provide planned positions and orientations of the planar surfaces 102-110 and the pilot holes 120 as shown in FIG. 1. The surgical plan may be generated based on medical imaging, 3D modeling, surgeon input, etc.

At step 304, one or more control boundaries, such as haptic objects, are defined based on the surgical plan. The one or more haptic objects may be one-dimensional (e.g., a line haptic), two dimensional (i.e., planar), or three dimensional (e.g., cylindrical, funnel-shaped, curved, etc.). The haptic objects may represent planned bone modifications (e.g., a haptic object for each of the planar surfaces 102-110 and each of the pilot holes 120 shown in FIG. 1), implant components, surgical approach trajectories, etc. defined by the surgical plan. The haptic objects can be oriented and positioned in three-dimensional space relative to a tracked position of a patient's anatomy.

At step 306, a pose of a surgical tool is tracked relative to the haptic object(s), for example by the tracking system 222 described above. In some embodiments, one point on the surgical tool is tracked. In other embodiments, (e.g., in the example of FIGS. 4-5) two points on the surgical tool are tracked, for example a tool center point (TCP) at a tip/effective end of the surgical tool and a second interaction point (SIP) positioned along a body or handle portion of the surgical tool. In other embodiments, three or more points on the surgical tool are tracked. A pose of the surgical tool is ascertained relative to a coordinate system in which the one or more haptic objects are defined and, in some embodiments, in which the pose of one or more anatomical features of the patient is also tracked.

At step 308, the surgical tool is guided to the haptic object(s). For example, the display 264 of the surgical system 200 may display a graphical user interface instructing a user on how (e.g., which direction) to move the surgical tool and/or robotic device to bring the surgical tool to a haptic object. As another example, the surgical tool may be guided to a haptic object using a collapsing haptic boundary as described in U.S. Pat. No. 9,289,264, the entire disclosure of which is incorporated by reference herein. As another example, the robotic device may be controlled to automatically move the surgical tool to a haptic object.

In an embodiment where the robotic device is controlled to automatically move the surgical tool to the haptic object (referred to as motorized alignment or automated alignment), the robotic device may be controlled so that a duration of the alignment is bounded by preset upper and lower time thresholds. That is, across various instances of process 300 and multiple procedures, automated alignment in step 308 may be configured to always take between a first amount of time (the lower time threshold) and a second amount of time (the upper time threshold). The lower time threshold may be selected such that the robotic device moves over a long enough duration to be perceived as well-controlled and to minimize collision or other risks associated with high speed. The upper time threshold may be selected such that the robotic device moves over a short enough duration to avoid user impatience and provide improved usability. For example, the upper time threshold hold may be approximately five seconds in an example where the lower time thresholds is approximately three seconds. In other embodiments, a single duration setpoint is used (e.g., four seconds). Step 308 can include optimizing a path for the robotic device such that the step 308 ensures successful alignment to the haptic object while also satisfying the upper and lower time thresholds or duration setpoint.

At step 310, the robotic device is controlled to constrain movement of the surgical tool based on the tracked pose of the surgical tool and the poses of one or more haptic objects. The constraining of the surgical tool may be achieved as described above with reference to FIG. 2.

At step 312, exit of the surgical tool from the haptic object(s) is facilitated, i.e., to release the constraints of a haptic object. For example, in some embodiments, the robotic device is controlled to allow the surgical tool to exit a haptic object along an axis of the haptic object. In some embodiments, the surgical tool may be allowed to exit the haptic object in a pre-determined direction relative to the haptic object. The surgical tool may thereby be removed from the surgical field and the haptic object to facilitate subsequent steps of the surgical procedure. Additionally, it should be understood that, in some cases, the process 300 may return to step 308 where the surgical tool is guided to the same or different haptic object after exiting a haptic object at step 312.

Process 300 may thereby be executed by the surgical system 200 to facilitate a surgical procedure. Features of process 300 are shown in FIGS. 4-8 below according to some embodiments, and such features can be combined in various combinations in various embodiments and/or based on settings selected for a particular procedure. Furthermore, it should be understood that the features of FIGS. 4-8 may be provided while omitting some or all other steps of process 300. All such possibilities are within the scope of the present disclosure.

Figure 4:
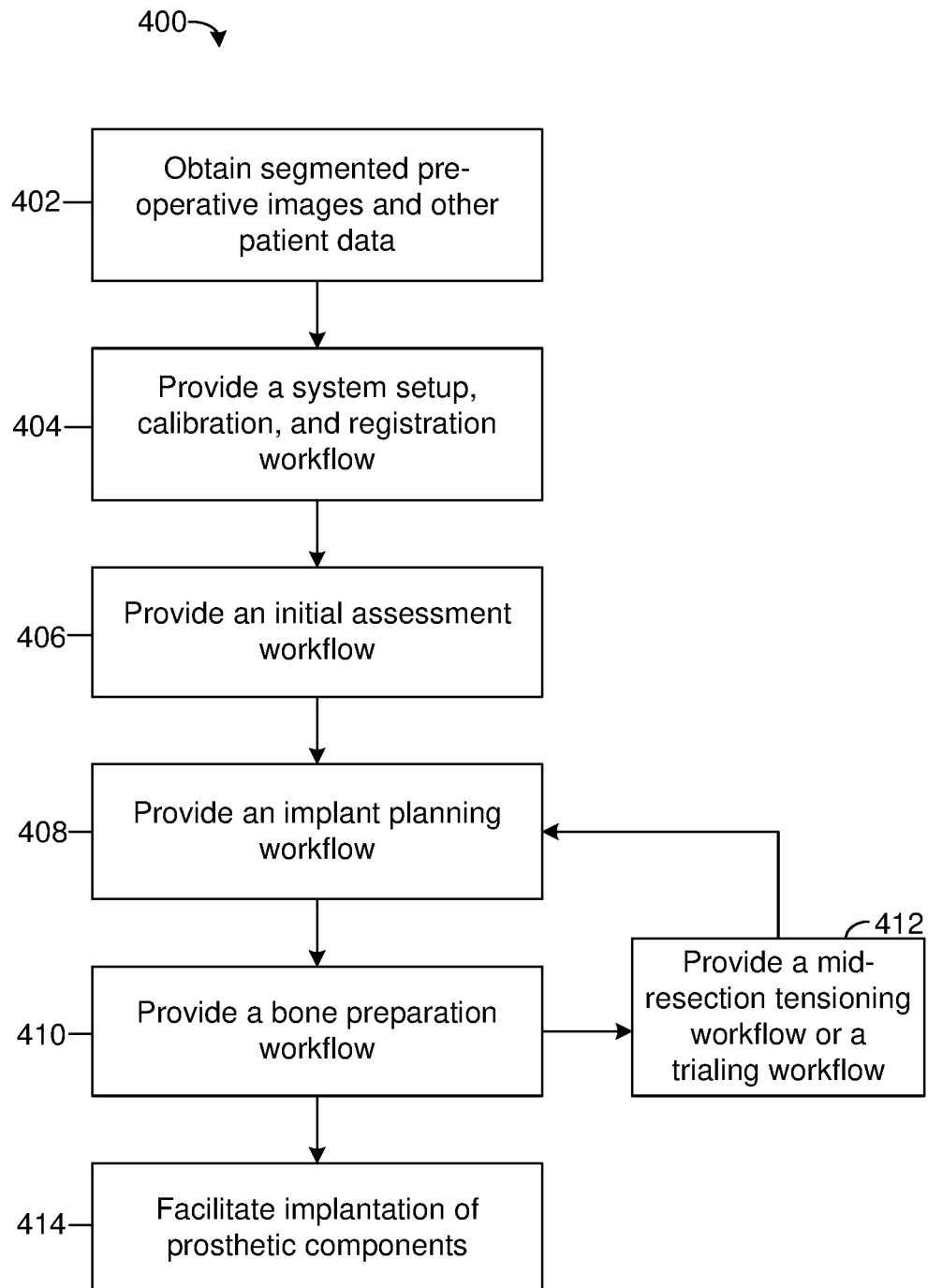
FIG. 4 is a flowchart of a second process that can be executed by the surgical system of FIG. 2, according to an exemplary embodiment.

Referring now to FIG. 4, a flowchart of a process 400 for facilitating surgical planning and guidance is shown, according to an exemplary embodiment. The process 400 may be executed by the surgical system 200 of FIG. 2, in some embodiments. In some cases, the process 300 is executed as part of executing the process 400.

At step 402, segmented pre-operative images and other patient data are obtained, for example by the surgical system 200. For example, segmented pre-operative CT images or MRI images may be received at the computing system 224 from an external server. In some cases, pre-operative images of a patient's anatomy are collected using an imaging device and segmented by a separate computing system and/or with manual user input to facilitate segmentation. In other embodiments, unsegmented pre-operative images are received at the computing system 224 and the computing system 224 is configured to automatically segment the images. The segmented pre-operative images can show the geometry, shape, size, density, and/or other characteristics of bones of a joint which is to be operated on in a procedure performed using process 400.

Other patient data can also be obtained at step 402. For example, the computing system 224 may receive patient information from an electronic medical records system. As another example, the computing system 224 may accept user input of patient information. The other patient data may include a patient's name, identification number, biographical information (e.g., age, weight, etc.), other health conditions, etc. In some embodiments, the patient data obtained at step 402 includes information specific to the procedure to be performed and the relevant pre-operative diagnosis. For example, the patient data may indicate which joint the procedure will be performed on (e.g., right knee, left knee). The patient data may indicate a diagnosed deformity, for example indicating whether a knee joint was diagnosed as having a varus deformity or a valgus deformity. This or other data that may facilitate the surgical procedure may be obtained at step 402.

At step 404, a system setup, calibration, and registration workflow is provided, for example by the surgical system 200. The system setup, calibration, and registration workflows may be configured to prepare the surgical system 200 for use in facilitating a surgical procedure. For example, at step 404, the computer system 224 may operate to provide graphical user interfaces that include instructions for performing system setup, calibration, and registrations steps. The computer system 224 may also cause the tracking system 222 to collect tracking data and control the robotic device 220 to facilitate system setup, calibration, and/or registration. The computer system 224 may also receiving tracking data from the tracking system 222 and information from the computer system 224 and use the received information and data to calibrate the robotic device 220 and define various geometric relationships between tracked points (e.g., fiducials, markers), other components of the surgical system 200 (e.g., robotic arm 232, surgical tool 234, probe), and virtual representations of anatomical features (e.g., virtual bone models).

The system setup workflow provided at step 404 may include guiding the robotic device 220 to a position relative to a surgical table and the patient which will be suitable for completing an entire surgical procedure without repositioning the robotic device 220. For example, the computer system 224 may generate and provide a graphical user interface configured to provide instructions for moving a portable cart of the robotic device 220 into a preferred position. In some embodiments, the robotic device 220 can be tracked to determine whether the robotic device 220 is properly positioned. Once the cart is positioned, in some embodiments the robotic device 220 is controlled to automatically position the robotic arm 232 in a pose suitable for initiation of calibration and/or registration workflows.

The calibration and registration workflows provided at step 404 may include generating instructions for a user to perform various calibration and registration tasks while operating the tracking system 222 to generate tracking data. The tracking data can then be used to calibrate the tracking system 222 and the robotic device 220 and to register the first fiducial tree 240, second fiducial tree 241, and third fiducial tree 242 relative to the patient's anatomical features, for example by defining geometric relationships between the fiducial trees 240-242 and relevant bones of the patient in the example of FIG. 2. The registration workflow may include tracking a probe used to touch various points on the bones of a joint. In some embodiments, providing the registration workflow may include providing instructions to couple a checkpoint (e.g., a screw or pin configured to be contacted by a probe) to a bone and tracking a probe as the probe contacts the checkpoint and as the probe is used to paint (i.e., move along, touch many points along) one or more surfaces of the bone. The probe can be moved and tracked in order to collect points in or proximate the joint to be operated upon as well as at other points on the bone (e.g., at ankle or hip for a knee surgery).

In some embodiments, providing the registration workflow includes generating instructions to move the patient's leg to facilitate collection of relevant tracking data that can be used to identify the location of a biomechanical feature, for example a hip center point. Providing the registration workflow can include providing audio or visual feedback indicating whether the leg was moved in the proper manner to collect sufficient tracking data. Various methods and approaches for registration and calibration can be used in various embodiments. Step 404 may include steps performed before or after an initial surgical incision is made in the patient's skin to initiate the surgical procedure.

At step 406, an initial assessment workflow is provided, for example by the surgical system 200. The initial assessment workflow provides an initial assessment of the joint to be operated upon based on tracked poses of the bones of the joint. For example, the initial assessment workflow may include tracking relative positions of a tibia and a femur using data from the tracking system while providing real-time visualizations of the tibia and femur via a graphical user interface. The computing system 224 may provide instructions via the graphical user interface to move the tibia and femur to different relative positions (e.g., different degrees of flexion) and to exert different forces on the joint (e.g., a varus or valgus force). In some embodiments, the initial assessment workflow includes determine, by the surgical system 200 and based on data from the tracking system 222, whether the patient's joint has a varus or valgus deformity, and, in some embodiments, determining a magnitude of the deformity. In some embodiments, the initial assessment workflow may include collecting data relating to native ligament tension or native gaps between bones of the joint. In some embodiments, the initial assessment workflow may include displaying instructions to exert a force on the patient's leg to place the joint in a corrected state corresponding to a desired outcome for a joint arthroplasty procedure, and recording the relative poses of the bones and other relevant measurements while the joint is in the corrected state. The initial assessment workflow thereby results in collection of data that may be useful for the surgical system 200 or a surgeon in later steps of process 400.

At step 408, an implant planning workflow is provided, for example by the surgical system 200. The implant planning workflow is configured to facilitate users in planning implant placement relative to the patient's bones and/or planning bone cuts or other modifications for preparing bones to receive implant components. Step 408 may include generating, for example by the computing system 324, three-dimensional computer models of the bones of the joint (e.g., a tibia model and a femur model) based on the segmented medical images received at step 402. Step 408 may also include obtaining three-dimensional computer models of prosthetic components to be implanted at the joint (e.g., a tibial implant model and a femoral implant model). A graphical user interface can be generated showing multiple views of the three-dimensional bone models with the three-dimensional implant models shown in planned positions relative to the three-dimensional bone models. Providing the implant planning workflow can include enabling the user to adjust the position and orientation of the implant models relative to the bone models. Planned cuts for preparing the bones to allow the implants to be implanted at the planned positions can then be automatically based on the positioning of the implant models relative to the bone models.

The graphical user interface can include data and measurements from pre-operative patient data (e.g., from step 402) and from the initial assessment workflow (step 406) and/or related measurements that would result from the planned implant placement. The planned measurements (e.g., planned gaps, planned varus/valgus angles, etc.) can be calculated based in part on data collected via the tracking system 222 in other phases of process 400, for example from initial assessment in step 406 or trialing or tensioning workflows described below with reference to step 412.

The implant planning workflow may also include providing warnings (alerts, notifications) to users when an implant plan violates various criteria. In some cases, the criteria can be predefined, for example related to regulatory or system requirements that are constant for all surgeons and/or for all patients. In other embodiments, the criteria may be related to surgeon preferences, such that the criteria for triggering a warning can be different for different surgeons. In some cases, the computing system 224 can prevent the process 400 from moving out of the implant planning workflow when one or more of certain criteria are not met.

The implant planning workflow provided at step 408 thereby results in planned cuts for preparing a joint to receive prosthetic implant components. In some embodiments, the planned cuts include a planar tibial cut and multiple planar femoral cuts, for example as described above with reference to FIG. 1. The planned cuts can be defined relative to the virtual bone models used in the implant planning workflow at step 408. Based on registration processes from step 404 which define a relationship between tracked fiducial markers and the virtual bone models, the positions and orientations of the planned cuts can also be defined relative to the tracked fiducial markers, (e.g., in a coordinate system used by the tracking system 222). The surgical system 200 is thereby configured to associate the planned cuts output from step 408 with corresponding planes or other geometries in real space.

At step 410, a bone preparation workflow is provided, for example by the surgical system 200. The bone preparation workflow includes guiding execution of one or more cuts or other bone modifications based on the surgical plan created at step 408. For example, as explained in detail above with reference to FIGS. 2-3, the bone preparation workflow may include providing haptic feedback which constrains the surgical tool 234 to a plane associated with a planned cut to facilitate use of the surgical tool 234 to make that planned cut. In other embodiments, the bone preparation workflow can include automatically controlling the robotic device 220 to autonomously make one or more cuts or other bone modifications to carry out the surgical plan created at step 408. In other embodiments, the bone preparation workflow comprises causing the robotic device 220 to hold a cutting guide, drill guide, jig, etc. in a substantially fixed position that allows a separate surgical tool to be used to execute the planned cut while being confined by the cutting guide, drill guide, jig, etc. The bone preparation workflow can thus include control of a robotic device in accordance with the surgical plan.

The bone preparation workflow at step 410 can also include displaying graphical user interface elements configured to guide a surgeon in completing one or more planned cuts. For example, the bone preparation workflow can include tracking the position of a surgical tool relative to a plane or other geometry associated with a planned cut and relative to the bone to be cut. In this example, the bone preparation workflow can include displaying, in real-time, the relative positions of the surgical tool, cut plane or other geometry, and bone model. In some embodiments, visual, audio, or haptic warnings can be provided to indicate completion or start of an event or step of the procedure, entry or exit from a state or virtual object, interruptions to performance of the planned cut, deviation from the planned cut, or violation of other criteria relating to the bone preparation workflow.

In some embodiments, step 410 is provided until all bone cuts planned at step 408 are complete and the bones are ready to be coupled to the implant components. In other embodiments, for example as shown in FIG. 4, a first iteration of step 410 can include performing only a portion of the planned cuts. For example, in a total knee arthroplasty procedure, a first iteration of step 410 can include making a tibial cut to provide a planar surface on the tibia without modifying the femur in the first iteration of step 410.

Following an iteration of the bone preparation workflow at step 410, the process 400 can proceed to step 412. At step 412 a mid-resection tensioning workflow or a trialing workflow is provided, for example by the surgical system 200. The mid-resection tensioning workflow is provided when less than all of the bone resection has been completed. The trialing workflow is provided when all resections have been made and/or bones are otherwise prepared to be temporarily coupled to trial implants. The mid-resection tensioning workflow and the trialing workflow at step 412 provide for collection of intraoperative data relating to relative positions of bones of the joint using the tracking system 222 including performing gap measurements or other tensioning procedures that can facilitate soft tissue balancing and/or adjustments to the surgical plan.

For example, step 412 may include displaying instructions to a user to move the joint through a range of motion, for example from flexion to extension, while the tracking system 222 tracks the bones. In some embodiments, gap distances between bones are determined from data collected by the tracking system 222 as a surgeon places the joint in both flexion and extension. In some embodiments, soft tissue tension or distraction forces are measured. Because one or more bone resections have been made before step 412 and soft tissue has been affected by the procedure, the mechanics of the joint may be different than during the initial assessment workflow of step 402 and relative to when the pre-operative imaging was performed. Accordingly, providing for intra-operative measurements in step 412 can provide information to a surgeon and to the surgical system 200 that was not available pre-operatively and which can be used to help fine tune the surgical plan.

From step 412, the process 400 returns to step 408 to provide the implant planning workflow again, now augmented with data collected during a mid-resection or trialing workflow at step 412. For example, planned gaps between implants can be calculated based on the intraoperative measurements collected at step 414, the planned position of a tibial implant relative to a tibia, and the planned position of a femoral implant relative to a femur. The planned gap values can then be displayed in an implant planning interface during step 408 to allow a surgeon to adjust the planned implant positions based on the calculated gap values. In various embodiments, a second iteration of step 408 to provide the implant planning workflow incorporates various data from step 412 in order to facilitate a surgeon in modifying and fine-tuning the surgical plan intraoperatively.

Steps 408, 410, and 412 can be performed multiple times to provide for intra-operative updates to the surgical plan based on intraoperative measurements collected between bone resections. For example, in some cases, a first iteration of steps 408, 410, and 412 includes planning a tibial cut in step 408, executing the planned tibial cut in step 410, and providing a mid-resection tensioning workflow in step 414. In this example, a second iteration of steps 408, 410, and 412 can include planning femoral cuts using data collected in the mid-resection tensioning workflow in step 408, executing the femoral cuts in step 410, and providing a trialing workflow in step 412. Providing the trialing workflow can include displaying instructions relating to placing trial implants on the prepared bone surfaces, and, in some embodiments, verifying that the trial implants are positioned in planned positions using the tracking system 222. Tracking data can be collected in a trialing workflow in step 412 relating to whether the trial implants are placed in acceptable positions or whether further adjustments to the surgical plan are needed by cycling back to step 408 and making further bone modifications in another iteration of step 410.

In some embodiments, executing process 400 can include providing users with options to jump between steps of the process 400 to enter a desired workflow. For example, a user can be allowed to switch between implant planning and bone preparation on demand. In other embodiments, executing process 400 can include ensuring that a particular sequence of steps of process 400 are followed. In various embodiments, any number of iterations of the various steps can be performed until a surgeon is satisfied that the bones have been properly prepared to receive implant components in clinically-appropriate positions.

As shown in FIG. 4, the process 400 includes step 414 where implantation of prosthetic components is facilitated. Once the bones have been prepared via step 410, the prosthetic components can be implanted. In some embodiments, step 414 is executed by the surgical system 200 by removing the robotic arm 232 from the surgical field and otherwise getting out of the way to allow a surgeon to fix the prosthetic components onto the bones without further assistance from the surgical system 200. In some embodiments, step 414 includes displaying instructions and/or navigational information that supports a surgeon in placing prosthetic components in the planned positions. In yet other embodiments, step 414 includes controlling the robotic arm 232 to place one or more prosthetic components in planned positions (e.g., holding a prosthetic component in the planned position while cement cures, while screws are inserted, constraining an impaction device to planned trajectory). Process 400 can thereby result in prosthetic components being affixed to modified bones according to an intraoperatively updated surgical plan.

Figure 5:
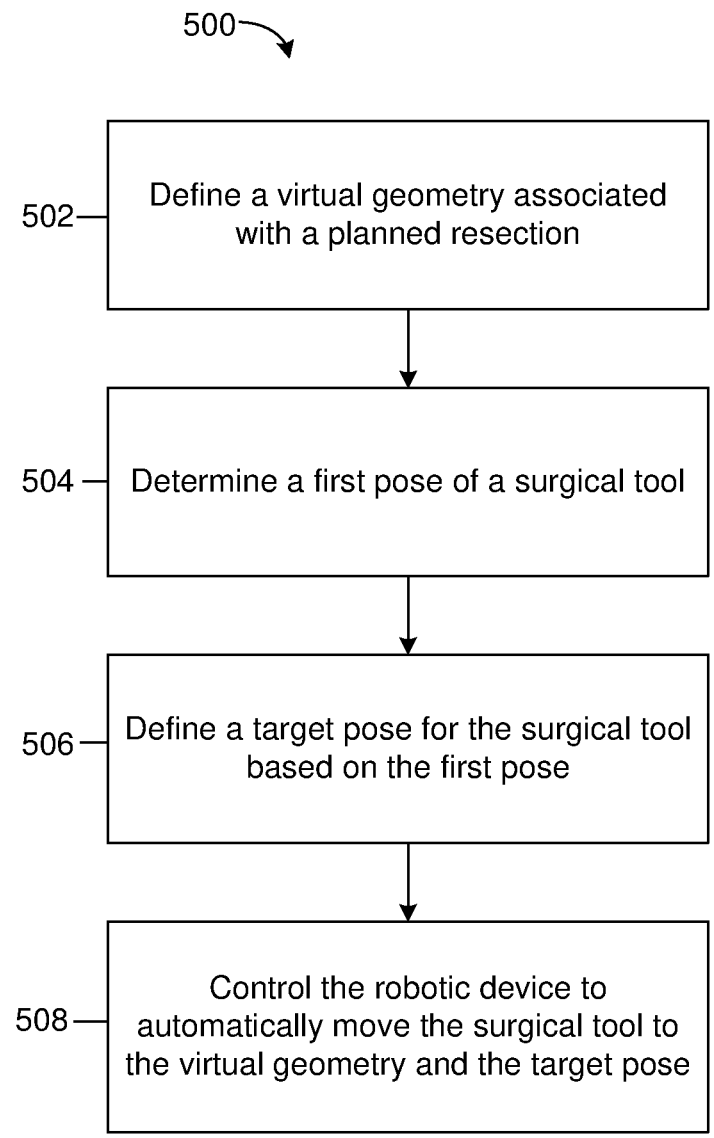
FIG. 5 is a flowchart of a process for controlling a robotic device to facilitate initiation of a bone resection, according to an exemplary embodiment.

Referring now to FIG. 5, a flowchart of a process 500 is shown, according to an exemplary embodiment. The process 500 can be executed by the surgical system 200 of FIG. 2, for example. The process 500 can be implemented as part of the bone preparation workflow of step 410 and/or as part of step 308 of FIG. 3, in various embodiments.

At step 502, a virtual geometry associated with a planned resection is defined. The virtual geometry may be haptic object or other control object as described above. The virtual geometry may be a line, plane, surface, volume, etc. in various embodiments. For example, the virtual geometry may be plane along which a surgical tool (e.g., saw) can be moved to cut a bone in order to execute the planned resection. The virtual geometry can be defined relative to a bone (or other object) which is to be modified by the planned resection, for example in a three-dimensional coordinate system used by a tracking system.

At step 504, a first pose of a surgical tool is determined. Determining the first pose includes determining an orientation of the surgical tool, for example the surgical tool 234 coupled to the robotic arm 232 in the surgical system 200 of FIG. 2. The first pose can be a current pose of the surgical tool at a particular time. For example, step 504 can be executed to determine the first pose as the current pose of the surgical tool in response to a user input, for example a user request to initiate automated alignment to a plane. In various such examples, step 504 can be executed in response to a user engaging an input device (e.g., trigger, foot pedal, button), making a selection on a graphical user interface, issuing a voice command, or providing some other input to the surgical system.

In other examples, step 504 is executed in response to an interruption of an ongoing bone preparation, for example as described in detail below with reference to FIG. 11. Various types of interruptions are possible. For example, an interruption may be caused by occlusion of the tracking system 222. In the example of FIG. 2, the occlusion can be caused by a blocking of the line-of-site between the detector device 246 and one or more of the fiducial trees 240-242, which can stop the tracking system 222 from being able to track relative positions of the bones and the surgical tool. As another example, an interruption may be caused by deviation of the surgical tool from a virtual object, for example caused by external forces on the surgical tool. Various other error conditions during bone preparation can cause interruptions, in various embodiment, and may trigger execution of step 504.

At step 506, a target pose is defined for the surgical tool based on the first pose. The first pose is an input to a function or logic which outputs the target pose. In some examples, step 506 includes categorizing the first pose into one of two or more categories, for example as described with reference to FIG. 6 below. In some examples, step 506 includes isolating one or more components of the first pose and defining the target pose based on the one or more isolated components (e.g., such that the target pose is not affected by other components of the pose). For example, step 506 can include determining an angle of the first pose in a first plane relative to a particular direction in that plane. The plane may correspond to a haptic plane associated with a planned resection. In such an example, step 506 can include determining an angle in the plane relative to a reference direction in that plane which is made by the surgical tool when in the first pose, and using that angle as an input to logic which outputs the target pose. An example of such an embodiment is illustrated at least in FIGS. 8-9 and 12-13 and described in detail with reference thereto below.

In some embodiments, the target pose defined at step 506 includes a position at the virtual geometry, for example on a haptic plane associated with a planned bone resection. In such embodiments, the position of the target pose within or along the virtual object may be variable based on the first pose, for example as described with reference to FIG. 10 below. Other components of the target pose (i.e., orientations in one or more degrees of freedom) can also be variable as a function of the first pose. As one example embodiment, the target pose may be defined so that it always lies in a predefined plane (e.g., a haptic plane) while also having an angle in the plane which varies as a function of the first pose and/or a position in the plane which varies as a function of the first pose.

At step 508, the robotic device is controlled to automatically move the surgical tool to the virtual geometry and the target pose. Automated motion can be initiated in response to a user input, for example engagement or disengagement of an input device such as a trigger, pedal, button, etc., or a voice command or other input. In some embodiments, a user action which causes initiation of step 504 also causes initiation of step 508.

Step 508 can include controlling motors of the robotic arm 232 so that the joints of the robotic arm 232 articulate to move the surgical tool 234 to the target pose and to the virtual geometry. Step 508 can include causing both translation and rotation of the surgical tool, such that automated motion of the surgical tool in multiple degrees of freedom is provided at step 508. The surgical tool is thereby automatically moved from a starting pose (which may or may not be the first pose determined in step 504 depending upon the implementation of a particular embodiment) to the target pose.

In some embodiments, step 508 includes planning a path for the automated movement of the robotic arm 232. For example, path planning can be executed to avoid obstacles and/or minimize a risk of collision with other objects proximate the robotic arm 232. In some embodiments, the path and a velocity along the path is determined such that automated movement the surgical tool to the target pose in step 508 is performed successfully in a duration of time within a range of acceptable durations and/or matching a preset duration. The range of acceptable durations and/or preset duration can be selected such that automated movement in step 508 is sufficiently slow to mitigate potential collisions risks and to provide the user with confidence that the automated alignment is well-controlled by the surgical system 200, while also keeping the automated movement in step 508 sufficiently quick so as to provide a high degree of usability and efficiency to process 500. For example, in some cases, step 508 can be confined to be performed over a duration in a range between three and five seconds or for a target duration of four seconds. In other embodiments, the automated movement of the surgical tool is provided with a preset speed or a speed (i.e., magnitude of velocity) within a preset range.

A resection can then be performed using the surgical tool, for example by continuing to step 310 of FIG. 3 and/or executing step 410 of FIG. 4.

Figure 6:
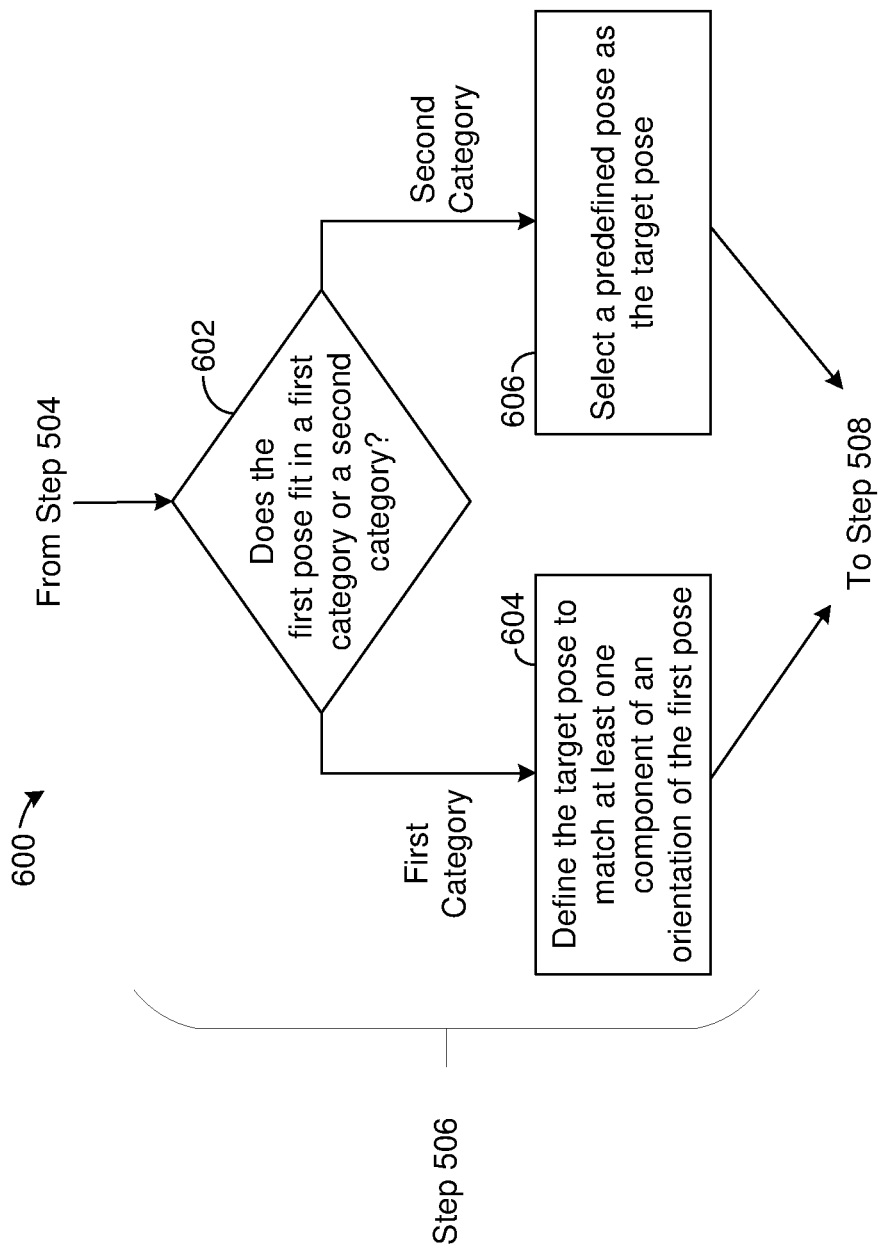
FIG. 6 is a flowchart of an example process for identifying a target pose as part of the process of FIG. 5, according to an exemplary embodiment.

Referring now to FIG. 6, a flowchart of a process 600 is shown, according to an exemplary embodiment. The process 600 is an example embodiment of step 506 of FIG. 5, and can be performed by the surgical system 200 in some embodiments. Process 600 is an example of how a target pose can be defined based on the first pose in step 506 of FIG. 5. FIG. 6 shows that the process 600 can fit between steps 504 and 508 of process 500.

At step 602, a determination is made of whether the first pose fits in a first category or in second category. In other embodiments, more categories can be used (e.g., three, four, five, etc.). The first category and the second category can be delineated such that any first pose either fits into the first category or the second category, but not both. The first pose can be processed and compared to one or more criteria to determine whether the first pose fits in the first category or the second category.

As one example, the first category and the second category can be delineated by whether the surgical tool points at least partially in a given direction when in the first pose. For example, the first category may be defined to include poses where the first tool points at least partially in the given direction, while the second category is defined as including only poses where the surgical does not even partially point in the given direction. In some embodiments, the first category corresponds to poses where the surgical tool points at least partially in a medial-to-lateral direction, whereas the second category corresponds to poses where the surgical tool does not point in the medial-to-lateral direction (e.g., points at least partially in a lateral-to-medial direction). To make such a determination in step 602, the first pose can be processed to isolate a particular component of the first pose (e.g., an angle in at least one degree of freedom, a component value of a vector corresponding to a relevant coordinate direction) which is indicative of whether the surgical tool points at least partially in the given direction.

As shown in FIG. 6, if the first pose fits in a first category, the process proceeds to step 604 where the target pose is determined in a first way, while if the first pose fits in the second category, the process proceeds to step 604 where the target pose is determined in a second way. In the example shown in FIG. 6, if the first pose fits in the first category, than the target pose is defined to match at least one component of an orientation of the first pose at step 604. For example, the target pose can be defined to be parallel to the first pose. As another example, the target pose may be selected so as to be at the same angle relative to a medial-to-lateral direction of the joint as the first pose. Other examples of how at least one component of the orientations can be matched are shown in following figures and described in detail with reference thereto.

Accordingly, when the starting pose is in the first category, the target pose varies as a continuous function of the first pose within the first category. FIG. 6 shows that, when the first poses fits in the second category, then the target pose is selected to be a predefined pose at step 606. That is, in this example, the target pose is always the same if the first pose is in the second category. For example, the predefined pose may lie in a predefined haptic plane associated with a planned resection, may be orthogonal to a medial-to-lateral direction of the joint, and may correspond to a preset distance from a bone or other object for resection. Other predefined poses can be used in various implementations.

Figure 8:
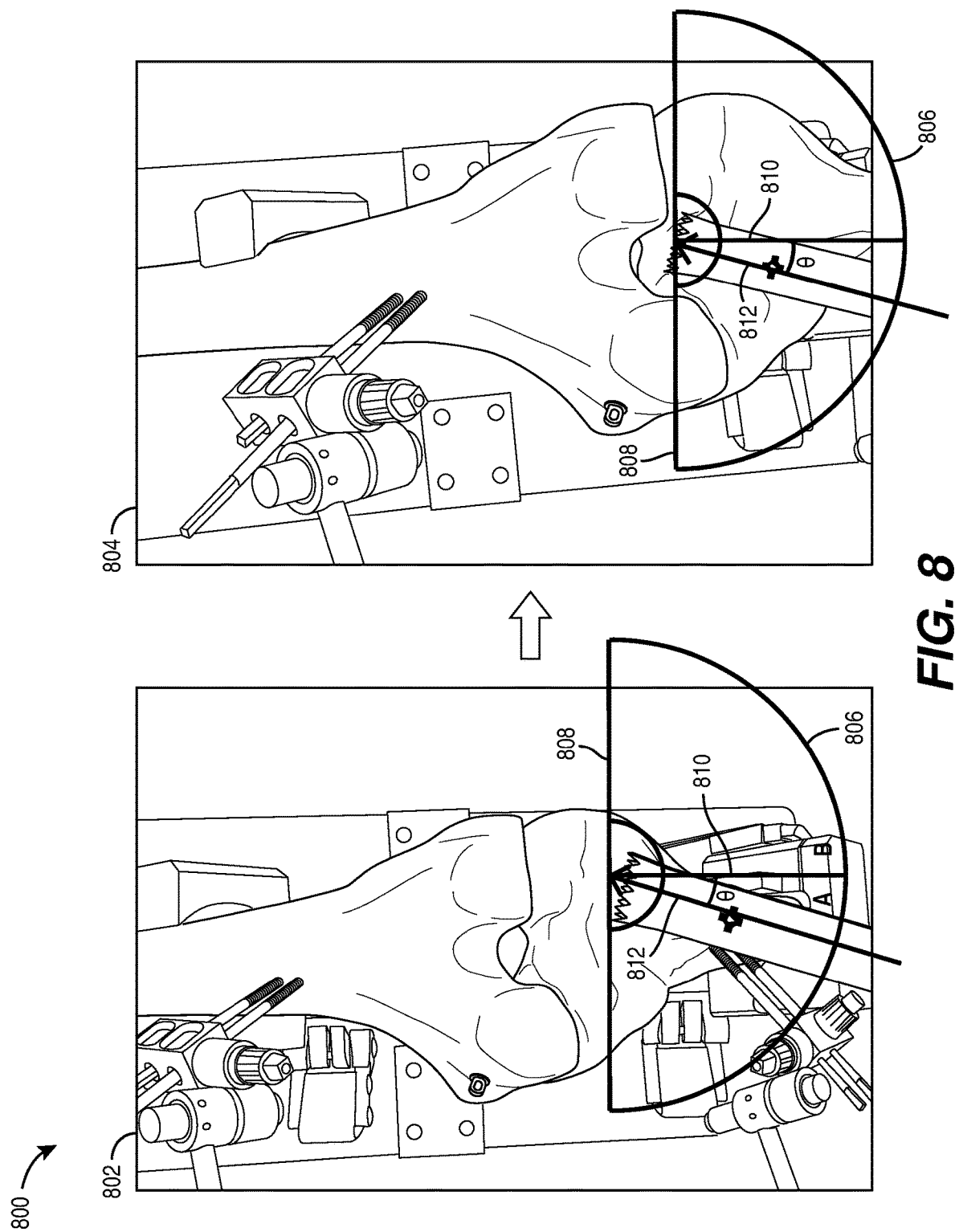
FIG. 8 is another illustration depicting an example implementation of the processes of FIGS. 5-6, according to an exemplary embodiment.
Figure 9:
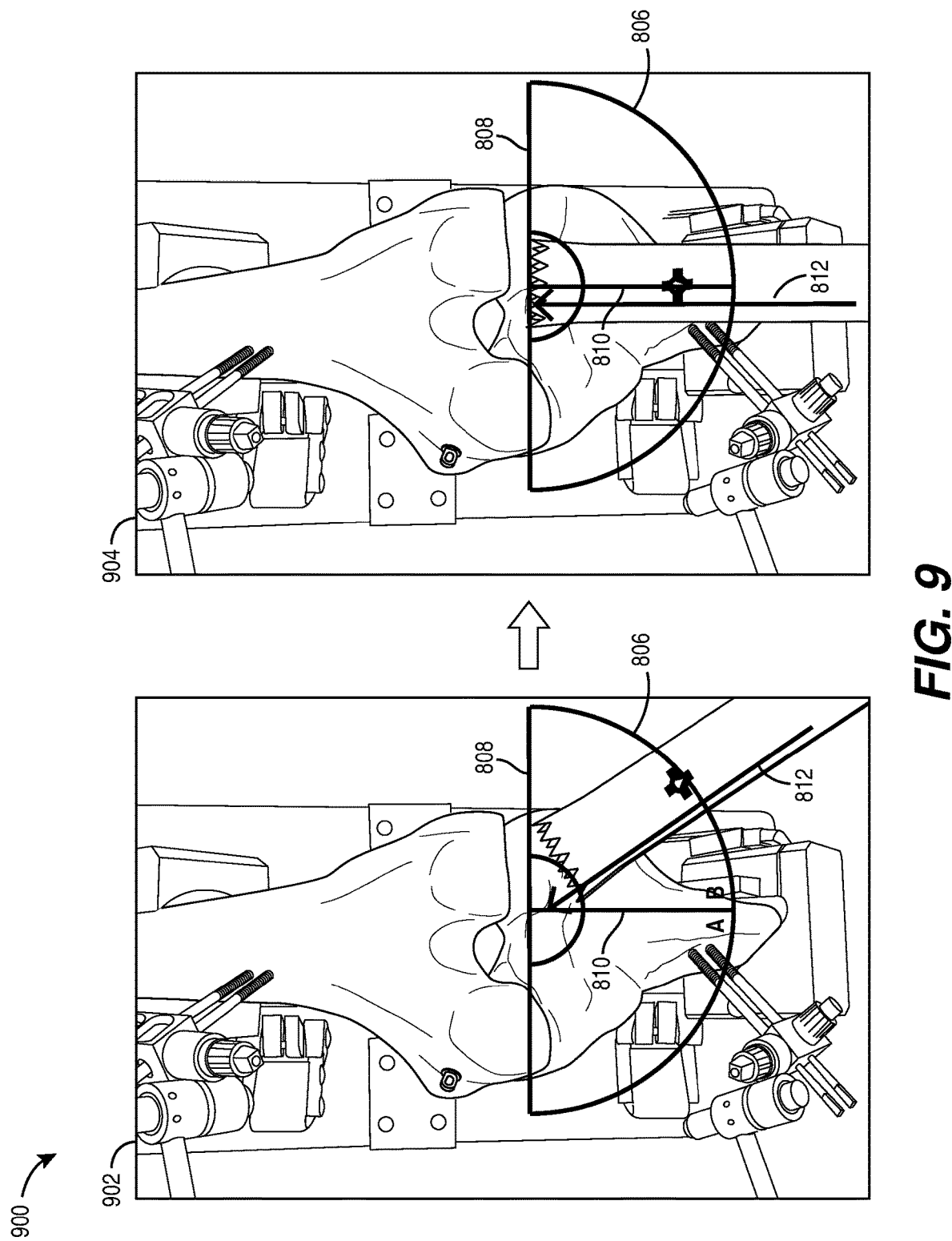
FIG. 9 is yet another illustration depicting an example implementation of the processes of FIGS. 5-6, according to an exemplary embodiment.

The target pose is thus defined in either step 604 or step 606 to conclude process 600. Process 500 can proceed to step 508, where a robotic device is controlled to automatically move the surgical tool to the target pose as described above. One advantage of process 600 is that it allows the automated movement in step 508 to be customized based on how the surgical tool is arranged when the first pose is determined. For example, in some embodiments the surgical tool can be manipulated by a user to change the pose of the surgical tool before the first pose is determined in step 504 of process 500. The user may thus be able to cause the first pose to fall into the first category or the second category, depending on the user's preferences for how the target pose should be defined in process 600. The automated movement in step 508 is thereby customizable, in some scenarios, by the user based on how the user orients the surgical tool prior to initiating the automated movement. Examples of such scenarios are shown in FIGS. 7-9 and described with reference thereto in the following passages.

Figure 7:
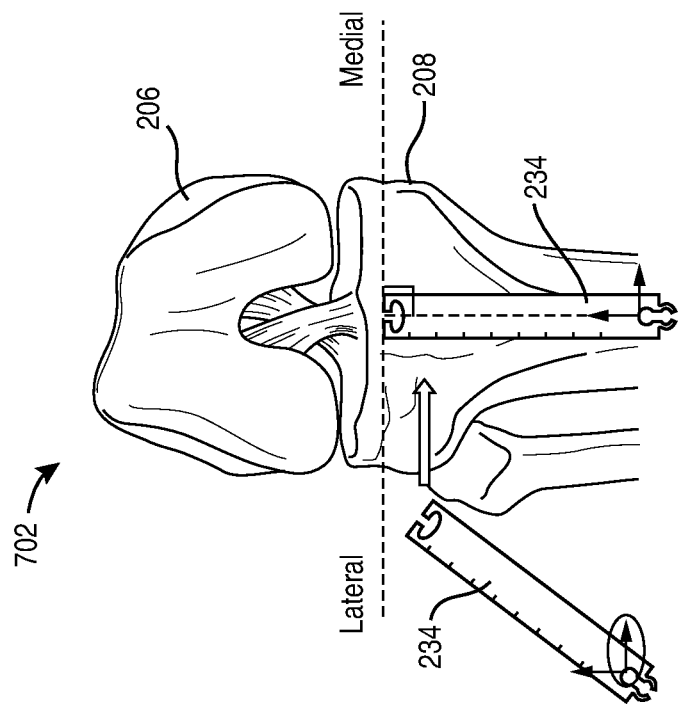
FIG. 7 is an illustration depicting an example implementation of the processes of FIGS. 5-6, according to an exemplary embodiment.
Figure 7:
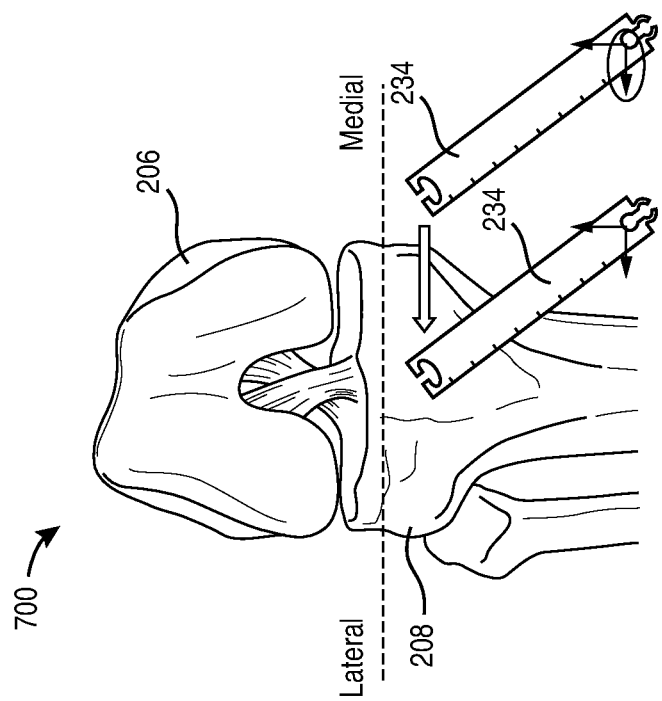

Referring now to FIG. 7, a first illustration of a possible implementation of process 500 and process 600 is shown, according to an exemplary embodiment. The illustration of FIG. 7 includes a first scenario 700 and a second scenario 702. Both scenarios 700 and 702 show a joint including a femur 206 and a tibia 208. Both scenarios 700 and 702 also illustrate the surgical tool 234 being automatically moved from a first pose to a target pose as indicated by arrows at the distal tips of the surgical tools 234. With reference to FIG. 6, scenario 700 provides an example of a first pose that fits in the first category such that step 604 is executed, while scenario 702 provides an example of a first pose that fits in the second category such that step 606 is executed.

In the first scenario 700 (the left side of FIG. 7), the surgical tool 234 is shown as having a first pose where the surgical tool points partially in a medial-to-lateral direction of a joint. This directional component of the pose of the surgical tool is circled in the illustration of the first scenario 700. In this example, because the surgical tool points at least partially in the medial-to-lateral direction of the joint in the first pose, the first pose is categorized as belonging to a first category so that step 604 is executed. As in process 600, in the first category the target pose is defined to at least partially match the first pose. In the example first scenario 700 shown in FIG. 7, the target pose is parallel to the first pose. Thus, in the automated movement shown by the solid arrow pointing in the medial-to-lateral direction, the surgical tool 234 is translated to a starting position for a resection while preserving the orientation of the surgical tool 234 from the starting pose.

In the second scenario 702 (the right side of FIG. 7), the surgical tool 234 is shown as having a first pose where the surgical tool points does not point in a medial-to-lateral direction of a joint, but rather points at least partially in the opposite, lateral-to-medial direction of the joint. This directional component is circled in the illustration of the second scenario 704, and may be understood as a negative value in the medial-to-lateral direction. In this example, because the surgical tool does not point at least partially in the (positive) medial-to-lateral direction, the first pose is categorized in the second category so that step 606 is executed. As shown in FIG. 7, the target pose is defined in step 606 as a predefined pose which is orthogonal to the medial-to-lateral direction and centered on the joint. In scenario 702, the surgical tool is illustrated as being automatically translated and rotated into this target pose.

Referring now to FIGS. 8-9, additional illustrations of example implementations of processes 500 and 600 are shown. FIG. 8 shows a third scenario 800 in a storyboard style illustration including a first frame 802 and a second frame 804, while FIG. 9 shows a fourth scenario 900 in a storyboard style illustration including a third frame 902 and a fourth frame 904. The first frame 802 shows the first pose in the third scenario 800, while the third frame 902 shows the first pose in the fourth scenario 900. The result of automated alignment to a target pose is shown at the second frame 804 and the fourth frame 904.

FIGS. 8-9 show a reference frame 806 which is used to categorize the first pose and to define the target pose in the example implementation of FIG. 6 shown in FIGS. 8-9. The reference frame 806 as illustrated includes a first line 808 which extends along a medial-to-lateral or lateral-to-medial direction of the joint, for example defined based in part on geometry of the tibia 208 and/or femur 206. The reference frame 806 is also shown as including a second line 810 orthogonal to the first line 808. The first line 808 and the second line 810 lie in a plane, for example a plane parallel to a planned cut or at a preset angle (e.g., orthogonal) relative to an axis of the joint, the tibia 208, or the femur 206.

The reference frame 806 is illustrated as aligned with a distal end of a projection 812 of the surgical tool 234 so that an angle $\theta$ is formed between the projection 812 of the surgical tool 234 and the second line 810. The second line 810 is shown as dividing the reference frame into a category A and category B. In the example shown, the first pose is characterized as falling into a first category (category A) if the projection 812 lies in the region to the left of the second line 810 from the perspectives of FIGS. 8 and 9 and as falling into a second category (category B) if the projection 812 lies in the region to the right of the second line as illustrated.

In scenario 800, the first pose is categorized in category A because the projection 812 of the surgical tool lies in the section of the reference frame 806 labeled as category A. In the example shown, this corresponds to a decision in process 600 to move to step 606 where the target pose is determined at least in part based on the first pose. In the example of FIG. 8, this entails defining the target pose such that the angle θ between the projection 812 of the surgical tool 234 onto the reference frame 806 and the second line 810 is preserved. Accordingly, when the robotic device 220 is controlled to provide automated movement of the surgical tool 234 from the first pose shown in frame 802 to the target pose shown in frame 804, the angular orientation of the surgical tool 234 in the reference frame 806 is substantially the same at the beginning and end of the automated movement (although it may deviate during the automated movement in some embodiments).

In scenario 900, the first pose is categorized in category B because the projection 812 of the surgical tool lies in the section of the reference frame 806 labeled as category B. In the example shown, this corresponds to a decision in process 600 to move to step 604 where the target pose is assigned to be a preset pose. That is, the target pose is the same for any first pose within category B in this example. As shown in FIG. 9, the surgical tool 234 is moved from the first pose shown in the first frame 902 to a target pose where the projection 812 of the surgical tool 234 is orthogonal to the first line 808 and parallel with the second line 810. In some embodiments, the surgical tool 234 itself lies in the same plane as the reference frame 806 in the target pose of frame 904 of the fourth scenario 900.

FIGS. 7-9 thereby illustrate several scenarios that may be provided using processes 500 and 600 in various implementations. Variations on these examples and scenarios are also within the scope of the present application. For example, the second line 810 which divides category A from category B may be at a different angle relative to the first line 808 in various embodiments. As another example, three or more categories associated different logic for defining a target pose are used.

Figure 10:
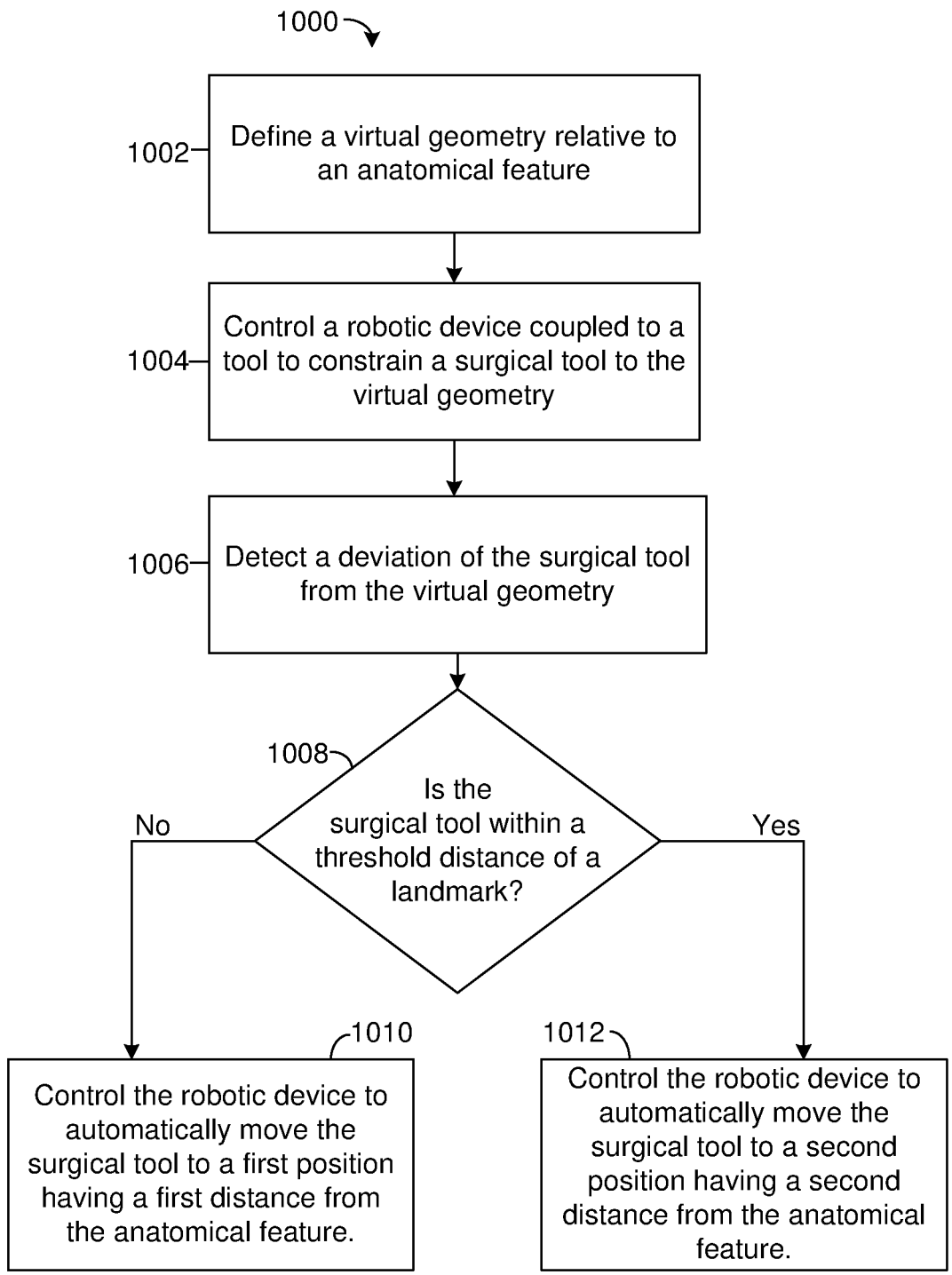
FIG. 10 is a flowchart of a process for recovery alignment during bone preparation that can be executed by the surgical system of FIG. 2, according to an exemplary embodiment.
Figure 11:
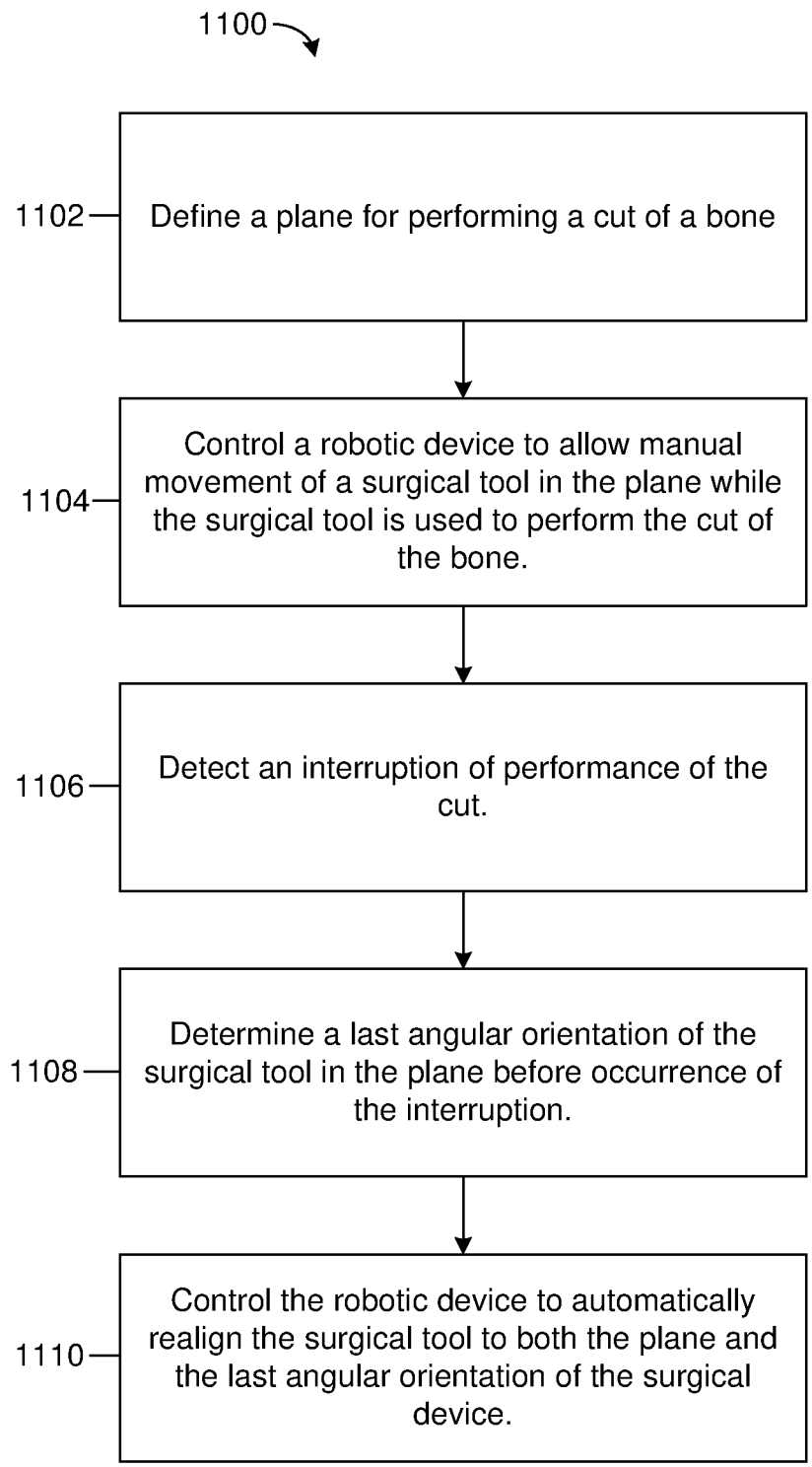
FIG. 11 is a flowchart of another process for recovery alignment during bone preparation that can be executed by the surgical system of FIG. 2, according to an exemplary embodiment.

Referring generally to FIGS. 10-11, flowcharts of a process 1000 and a process 1100 are shown, according to an exemplary embodiment. The processes 1000 and/or 1100 can be implemented as parts of (or as an addition to) process 300 or process 400, and may be used in variations of process 500. The processes 1000 and 1100 can be executed by the surgical system 200 in some embodiments.

The process 1000 of FIG. 10 and the process 1100 of FIG. 11 relate to realignment of a tool to a virtual geometry after a deviation from the virtual geometry and/or an interruption in performance of a bone resection. This realignment can be referred to herein as recovery alignment. The systems and methods described herein provide for efficiently, user-friendly, and reliable recovery alignment which can improve the user experience, reduce surgical operation times, and otherwise improve the operation of a robotically-assisted surgery system. For example, these solutions provide improvements relative to previous solutions in which an interruption or deviation would require the surgical tool to be pulled far away from the planned resection before an initial alignment process (e.g., step 308) is performed again in order to restart execution of a cut, which may be relatively time-consuming and more frustrating and cumbersome for users.

Referring particularly to FIG. 10, at step 1002, a virtual geometry is defined relative to an anatomical feature. The virtual geometry may be control object or haptic object, for example planar object corresponding to a planned bone resection. Any of the various examples of virtual geometries described herein can be used in various embodiments. Step 1002 can correspond to step 304 of process 300 and may be part of step 408 of process 400.

At step 1004, a robotic device is controlled to constrain a surgical tool to the virtual geometry. Step 1004 can be executed substantially the same as step 310 of FIG. 3 described in detail above. Step 1004 can include controlling the robotic device to provide force feedback which resists the surgical tool from leaving the virtual geometry, while allowing a user to manually manipulate the surgical tool to move the surgical tool within the virtual geometry. For example, step 1004 can include allowing manual movement in a haptic plane while controlling the robotic device to provide forces which resist deviation of the surgical tool from the haptic plane.

The forces constraining the surgical tool to the virtual geometry in step 1004, however, may resist deviation from the haptic plane but, in the examples of primary relevance to process 1000, may not be sufficient to completely prevent deviations from the haptic plane. For example, a surgeon may exert an external force on the surgical tool which exceeds the force feedback by the robotic device, thereby causing the surgical tool to deviate from the virtual geometry.

A deviation of the surgical tool from the virtual geometry may also be tied to some other cause, for example a movement of the anatomical feature. The virtual geometry may be defined relative to a tracked position of the anatomical feature, such that the virtual geometry moves when the anatomical feature moves. In such an example, movement of the anatomical feature without corresponding movement of the surgical tool could cause the virtual geometry to update such that the surgical tool is no longer within the virtual geometry. This and various other scenarios could cause deviation of the surgical tool from the virtual geometry during execution of step 1004.

At step 1006, a deviation of the surgical tool from the virtual geometry is detected. For example, data from the tracking system 222 can be used to determine that the surgical tool (e.g., a tool center point or one or more haptic interaction points) are not positioned at or within the virtual geometry. In some cases, a deviation is detected at step 1006 if the surgical tool is more than a threshold distance from the virtual geometry. In some cases, the deviation is detected at step 1006 if the surgical tool is misaligned from the virtual geometry, even if the surgical tool still at least partially touches or intersects the virtual geometry. In other embodiments, a different interruption of bone preparation is detected at step 1006 (see the description of process 1100 below for example interruptions).

Step 1006 can include interrupting bone preparation so that a patient's tissue is not cut, resected, or otherwise modified in a manner inconsistent with a surgical plan. For example, step 1006 can include causing an audible, haptic, or visual alert to be provided to a user indicating that a deviation has occurred in response to detecting the deviation. In some cases, step 1006 includes disabling the surgical tool in response to detecting the deviation. Accordingly, as a result of step 1006, bone preparation may be paused, and may remain paused until the surgical tool is realigned to the virtual geometry.

At step 1008, a determination is made of whether the surgical tool is within a threshold distance of a landmark. For example a distance between a tool center point of the surgical tool and the virtual geometry may be determined and compared to a threshold value. As another example, a distance between a tool center point of the surgical tool and the anatomical feature may be determined and compared to a threshold value. As various other examples, the distance used is between the surgical tool and another virtual point, line, surface, or volume in a virtual reference frame. The determined distance can then be compared to a threshold distance (e.g., maximum value) to determine whether the surgical tool is within the threshold distance of the landmark (e.g., less than the maximum value).

If the distance between the tool and the landmark is greater than the threshold distance, process 1000 proceeds to step 1010 where the robotic device is controlled to automatically move the surgical tool to a first position having a first distance from the anatomical feature. Step 1010 can also include automatically realigning the surgical tool to the virtual geometry. If the distance between the tool and the landmark is less than the threshold distance, process 1000 proceeds to step 1012 where the robotic device is controlled to move the surgical tool to a second position having a second distance from the anatomical feature. Step 1012 can also include automatically realigning the surgical tool to the virtual geometry.

The second distance in step 1012 is preferably less than the first distance as in step 1010. In such examples, the surgical tool is automatically moved to a point relatively close to the landmark (e.g., to a bone to be cut) if the deviation leaves the surgical tool at less than a threshold distance of the landmark, and at a point relatively further away from the landmark (e.g., from the bone to be cut) if the deviation leaves the surgical tool at greater than a threshold distance from the landmark. Advantageously, this allows for quick, user-friendly automated recovery alignment in step 1012 to a point close to a cut when the surgical tool has only deviated from the virtual geometry by a small amount, while providing for a more conservative realignment to a point further from the cut when a deviation is more significant. These features can improve efficiency and overall operation time, while also improving usability of and trust in the surgical system.

In some cases, the process returns to step 1004 and continues to run until a cut is complete. Process 1000 thereby provides follow-on features that can be advantageous when provided with surgical system 200, process 300, or process 400 described in detail above.

Referring now particularly to FIG. 11, the process 1100 starts at step 1102 where a plane is defined for performing a cut of a bone. Other virtual objects can be defined in addition or in other embodiments. The plane can correspond to acceptable or intended positions for a surgical tool (e.g., saw) to pass through in order to executed a bone resection in accordance with a surgical plane.

At step 1104, a robotic device is controlled to allow manual movement of the surgical tool in the plane while the surgical tool is used to perform the cut of the bone. For example, the robotic device 220 of the surgical system 200 can be controlled to provide haptic feedback to a user manually forcing the surgical tool to move within the plane, as explained in detail above with reference to FIGS. 2-4.

With the surgical tool confined to a plane, the surgical tool can be allowed to translate in the plane and to rotate in the plane. Rotation in the plane here refers to rotation about a direction normal to the plane to change an angular orientation of the surgical tool in the plane (e.g., an angular orientation of a blade of a surgical saw or other cutting device). Through such rotation, the angular orientation of the surgical tool can change during execution of step 1104. For example, a surgeon may prefer to put the surgical tool in a first angular orientation while cutting a first section of bone (e.g., a first condyle) while a different angular orientation may be better suited for cutting a second section of the bone (e.g., a second condyle). The surgeon is thereby enabled to use an angular orientation in the plane suitable for a current subpart of the cut being executed, while the robotic device confines the surgical tool from deviating from the plane.

At step 1106, an interruption of performance of the cut is detected, caused, generated, or otherwise occurs. The interruption causes bone preparation to pause at least temporarily. Various types of interruptions are possible. For example, an interruption may be caused by occlusion of the tracking system 222. In the example of FIG. 2, the occlusion can be caused by a blocking of the line-of-site between the detector device 246 and one or more of the fiducial trees 240-242, which can stop the tracking system 222 from being able to track relative positions of the bones and the surgical tool. The interruption may be determine when one of the fiducial trees is not visible to the detector device 246 for more than a time limit. As another example, an interruption may be caused by deviation of the surgical tool from a virtual object, for example caused by external forces on the surgical tool. As another example, the interruption may be in response to a user input corresponding to a request to pause bone preparation (e.g., release or engagement of an input device such as a trigger or pedal, input to a graphical user interface, a voice command). As yet another example, if a velocity of the anatomy is detected to be greater than a threshold magnitude, an interruption is caused. As yet another example, if a velocity of the base of the robotic device is detected to be greater than a threshold magnitude, an interruption is caused. Various error conditions during bone preparation may also be detected at step 1106 to trigger an interruption. In some cases, step 1106 includes providing a visual, haptic, and/or audible alert indicating occurrence of the interruption. The alert may indicate the cause of the interruption and/or an option or instructions for resolving the interruption and restarting bone preparation.

At step 1108, in response to the interruption, a last angular orientation of the surgical tool in the plane before occurrence of the interruption is determined. This last angular orientation is the angle at which the surgeon was using the surgical tool in the plane as part of performing the bone preparation when the interruption occurred or was detected. Accordingly, the last angular orientation may correspond to a surgeon's preferred orientation for completing the subpart of the bone preparation which was being executed when the interruption occurred.

At step 1110, the robotic device is controlled to automatically realign the surgical tool to both the plane and to the last angular orientation of the surgical device. This may include translating or rotating the surgical to so that it lies in the plane and rotating the surgical tool so that the surgical tool returns to the last angular orientation of the surgical device determined in step 1108. As for other automated motions described herein, automated alignment in step 1110 can be initiated by a user input, for example engagement of an input device or other type of input as described herein.

Realignment to the plane in step 1110 enables the process 1100 to return to step 1104, where the surgical tool is confined to the plane to facilitate performance of the planned bone preparation.

Realignment to the last angular orientation in the plane in step 1110 provides an additional level of usability and efficiency for the surgeon, by returning the surgical tool the angular orientation in the plane which corresponds to the subpart of a bone preparation which was being performed at the time of the interruption. Step 1110 thereby facilitates the user in seamlessly restarting bone preparation as if the interruption had not occurred, without having to manually rotate the surgical tool in the plane back to a desired orientation. This aspect of process 1100 may thus be particular advantage in providing easy, efficient, and highly usable recovery alignment in response to an interruption of bone preparation, for example compared to another implementation where the surgical tool is always realigned to the same predetermined position and orientation.

Figure 13:
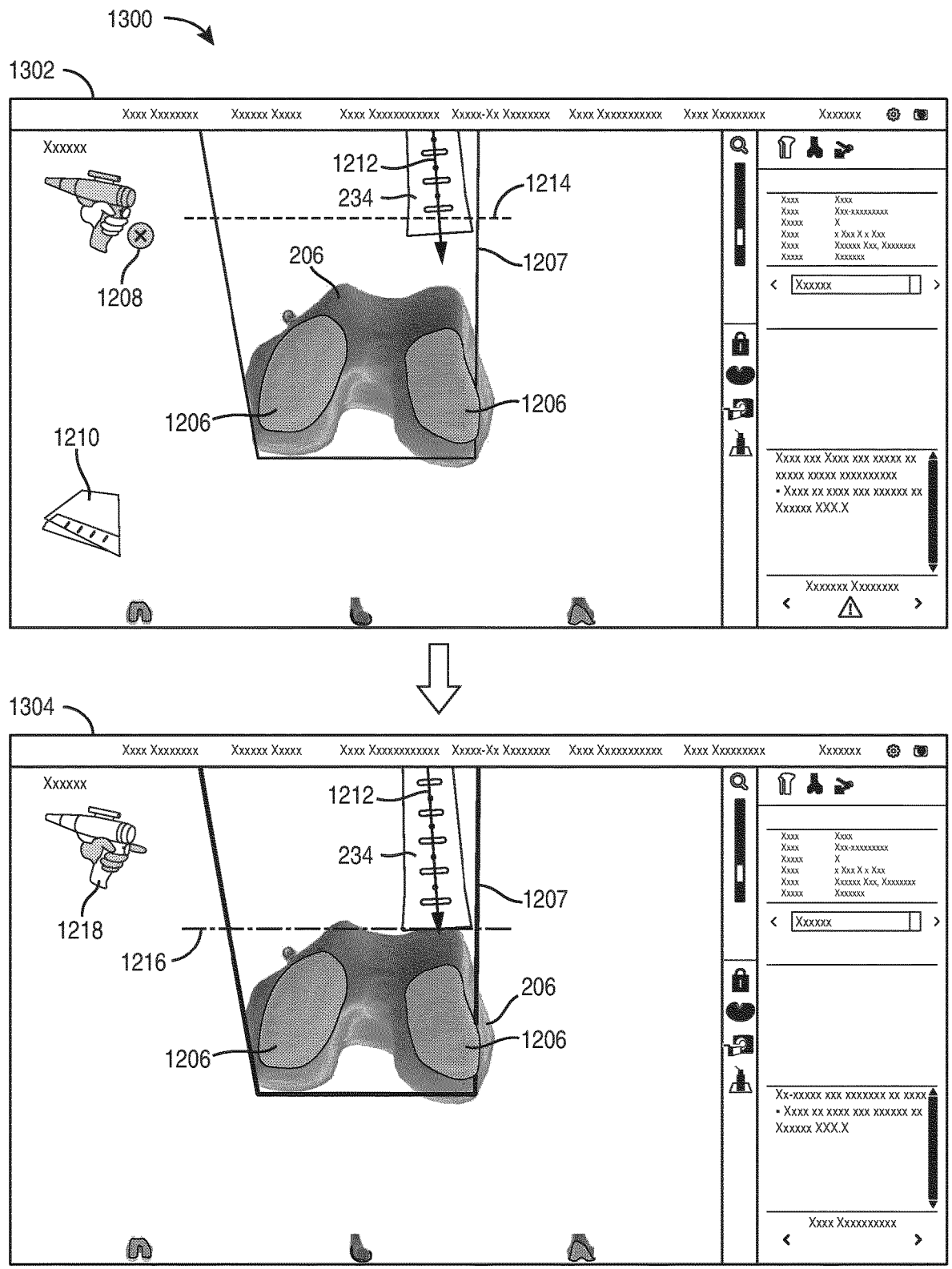
FIG. 13 is another illustration depending an example implementation of the processes of FIGS. 10-11, according to an exemplary embodiment.
Figure 14:
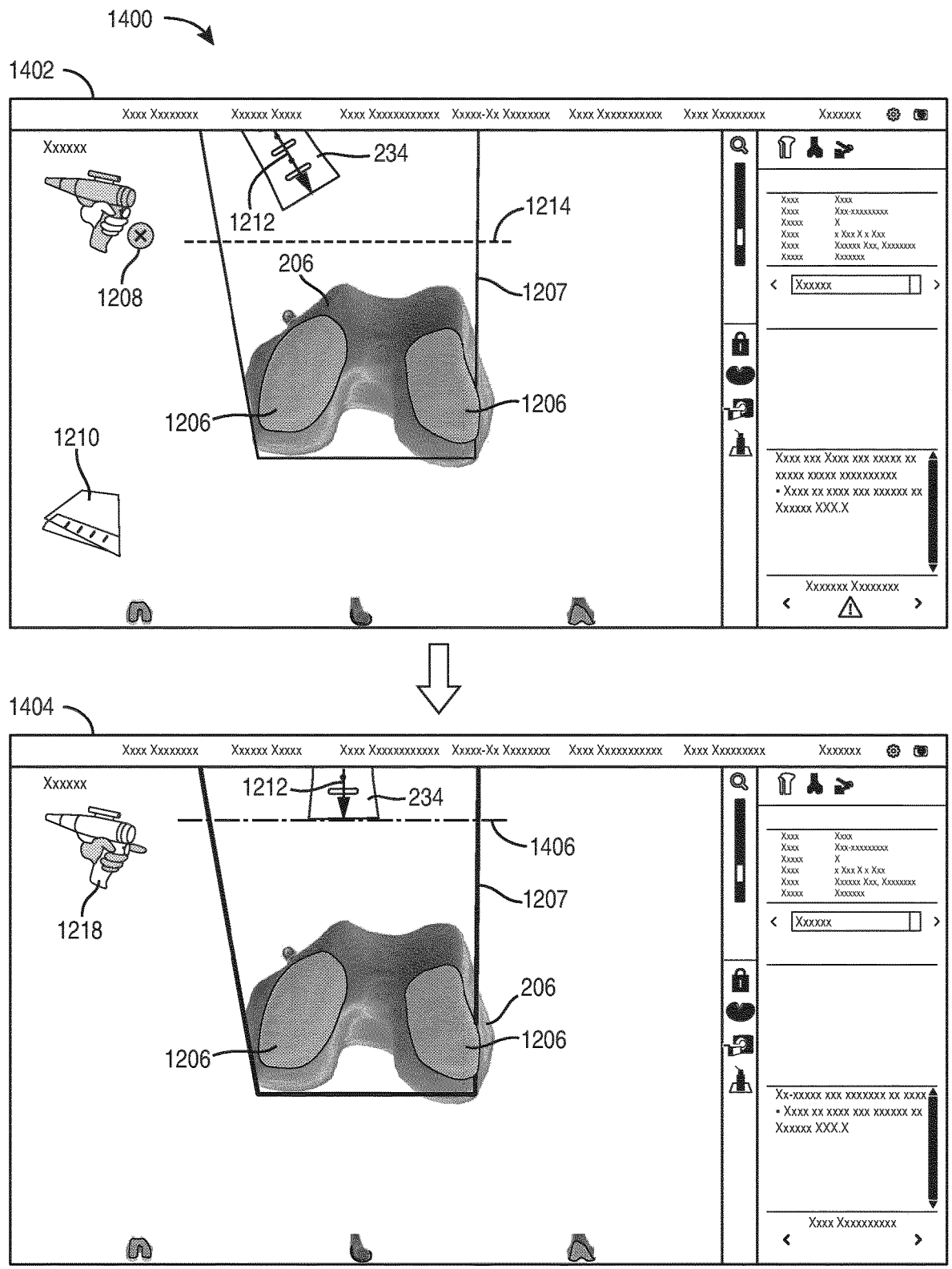
FIG. 14 is yet another illustration depending an example implementation of the processes of FIGS. 10-11, according to an exemplary embodiment.

Process 1000 and process 1100 thereby provide various advantages relating to recovery alignment of the surgical tool to a virtual geometry during use of the surgical system 200 in executing a planned bone preparation. Process 1000 and 1100 are both used during recovery alignment in some implementations. Example scenarios are shown in FIGS. 12-14 and described in the following passages.

Figure 12:
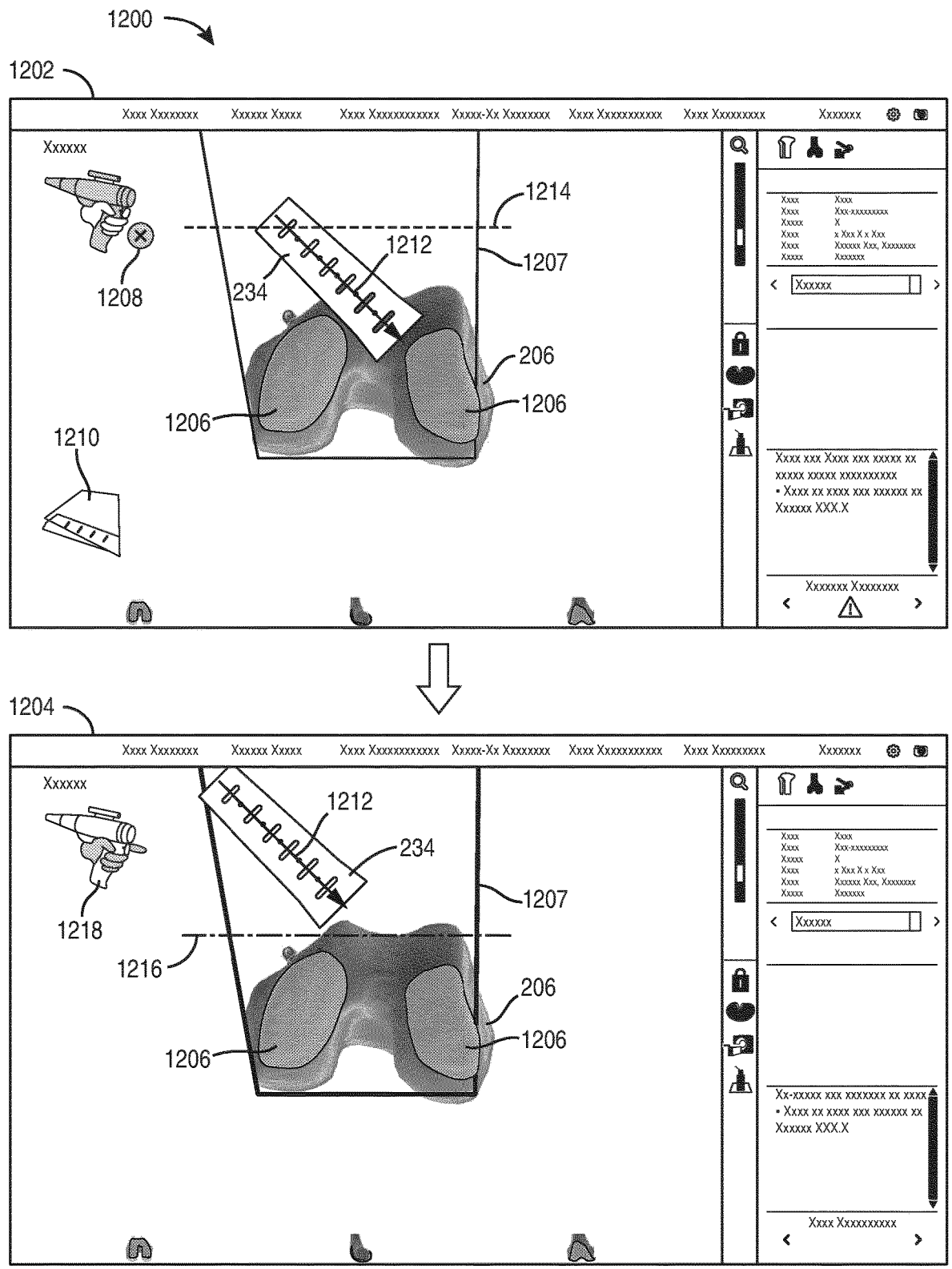
FIG. 12 is an illustration depending an example implementation of the processes of FIGS. 10-11, according to an exemplary embodiment.

Referring now to FIG. 12, a storyboard-style illustration 1200 including a first frame 1202 sequentially before a second frame 1204 is shown, according to an exemplary embodiment. The storyboard-style illustration 1200 shows an example where process 1000 and 1100 are executed in a combined manner. The first frame 1202 and the second frame 1204 show views in a graphical user interface that can be provided via the display 264 of the surgical system 200 during a bone preparation workflow (e.g., during step 410). The graphical user interface can be updated in real-time to show a current pose of the surgical tool 234 relative to a tracked anatomical structure (e.g., bone), shown as femur 206, by displaying a virtual representation of the surgical tool 234 relative to a virtual model of the femur 206. The graphical user interface can also indicate sections of bone to be removed, shown as planned resection volume 1206. The graphical user interface can also show a depiction of a virtual geometry used to confine the surgical tool 234 during bone preparation, shown in this example as haptic plane 1207.

In the first frame 1202, the graphical interface indicates that an interruption has occurred by displaying an interruption graphic 1208. The interruption graphic 1208 can be shown in red and with an "X" icon to provide the user with an intuitive understanding that the interruption graphic 1208 indicates that bone preparation is stopped or paused. The interruption graphic 1208 also shows a hand (e.g., a surgeon's hand) griping and handle and trigger of a surgical tool and/or of the robotic device to indicate that the user should engage or release the trigger, in the example shown. Other input devices, grips, handles, hand-pieces, etc. can be shown as may be suitable in various embodiments.

In the first frame 1202, the graphical interface also includes an icon which indicates and visualizes the cause of the interruption, in this example shown as a blade-off-plane icon 1210 indicating that the blade of the surgical tool 234 translated and/or rotated so as to be no longer aligned with the haptic plane 1207. The blade-off-plane icon 1210 is designed to illustrate the issue to users so that the user can easily and quickly understand the cause of the interruption, thereby reducing frustration and improving usability of the system. A blade-off-plane error as indicated by the blade-off-plane icon can be detected using data from the tracking system 222 and can be caused by external forces exceeding the force feedback provided by the robotic arm to constrain the surgical tool to the haptic plane 1207.

Accordingly, the first frame 1202 shows the position and orientation of the surgical tool 234 relative to the femur 206 and the haptic plane 1207 when an interruption and deviation occurs, and can thus correspond to step 1006 of process 1000 and step 1106 of process 1100. In the example of illustration 1200, the surgical tool 234 is at an angle in the haptic plane 1207 indicated by the arrow 1212 overlaid on the surgical tool 234 in FIG. 12. As described above with reference to process 1100, this angle can be determined in step 1108 for use in recovery alignment in step 1110.

In the first frame 1202, the surgical tool 234 is also proximate the femur 206, for example about to engage the planned resection volume 1206. The position of the surgical tool 234 in the first frame can be used to determine whether the surgical tool 234 is within a threshold distance of a landmark as in step 1006 of process 1000. In the example of the first frame 1202, the relevant distance is between the surgical tool and the bone, and a demarcation line 1214 is included to illustrate an example threshold distance. The demarcation line 1214 is illustrated away from the bone in a direction parallel to the haptic plane 1207 for the sake of example and for the ease of illustration in the drawings, but the threshold distance may also be measured in other directions or translational or rotational directions. For example, the distance from the bone, haptic plane, or other landmark used in a given implementation of step 1006 can be measured in a direction normal to the haptic plane. In such a case, the threshold distance assess a size, degree, extent, etc. of the blade-off-plane interruption which caused the interruption shown in the first frame 1202. The demarcation line 1214 may be further or closer to the bone in other embodiments. In the first frame 1202, the surgical tool 234 is between the demarcation line 1214 and the planned resection volume 1206, and is thus considered within the threshold distance in this example implementation of step 1008 of process 1000. In this example, process 1000 will thus proceed to step 1012.

To move from the first frame 1202 to the second frame 1204 in illustration 1200, the robotic device is controlled to provide automated recovery alignment in accordance with step 1012 of process 1000 and step 1110 of process 1000. That is, the second frame 1204 shows an updated view in the graphical user interface with the surgical tool 234 successfully realigned to the haptic plane 1207 through motorized movement of the robotic device 220. As shown, the blade-off-plane icon 1210 is removed, indicated resolution of the blade-off-plane error. Consistent with step 1110 of process 1100 detailed above, the surgical tool as realigned to the plane 1207 is also matched to the last angular orientation of the surgical tool in the plane. That is, the arrow 1212 indicating the angular orientation of the surgical tool in the second frame 1204 is parallel to how the arrow 1212 is shown in the first frame 1202. The user thus will not have to manually reorient the surgical tool in the plane to get back to where the interruption occurred in frame 1202.

In the second frame 1204, the surgical tool 234 has also been moved to a close-in landing line 1216. With reference to step 1012 described above, the close-in landing line 1216 is a second distance from the anatomical feature. In the example of FIG. 12, the surgical tool 234 is automatically moved further away from the planned resection volume 1206 in order to be positioned at the close-in landing line 1216, while still remaining proximate the femur 206 in order to facilitate a relatively quick restart of bone preparation. The second frame 1204 shows a restart icon 1218 which indicates to a user that an input device (e.g., a trigger proximate the surgical tool 234) can be selected to restart cutting of the bone with the surgical tool 234. The planned resection can then be accomplished using the surgical tool 234 confined to the haptic plane 1207 as described in detail above.

FIG. 13 shows another example scenario of recovery alignment, consistent with the implementation of process 1000 and process 1100 as in the example of FIG. 12. In particular, FIG. 13 shows a storyboard-style illustration 1300 including a first frame 1302 sequentially before a second frame 1304, according to an exemplary embodiment. As in FIG. 12, the first frame 1302 corresponds to occurrence of an interruption and deviation from the haptic plane 1207, and the second frame 1304 corresponds to the result of successful recovery alignment to the haptic plane.

In the graphical user interface as shown in the first frame 1302 of illustration 1300, the surgical tool 234 is further away from the femur 206 as compared to the example of FIG. 12, but is still closer than the threshold distance as indicated by the demarcation line 1214 in this example embodiment. Thus, as in FIG. 12, the process 1000 will proceed to step 1012, and the surgical tool will be automatically moved during recovery alignment to the same close-in landing line 1216 as in the second frame 1204 of illustration 1200. Accordingly, the second frame 1304 illustrates that the surgical tool is moved to the close-in landing line 1216, as an example of successful execution of process 1000. In this example, the automated recovery alignment in process 1000 draws the surgical tool closer to the femur 206 and the planned resection volume 1206. In some embodiments and in situations where the planned resection is already partially completed, the close-in landing line 1216 may be within the planned resection volume 1206.

The illustration 1300 also shows that the arrow 1212 indicating the angular orientation of the surgical tool in the haptic plane 1207 also remains at the same angle in the first frame 1302 and the second frame 1304, as an example of successful execution of process 1100. The example of illustration 1300 thereby puts the surgical tool in a position for bone preparation to be quickly and efficiently initiated.

FIG. 14 shows another example scenario of recovery alignment, consistent with the example implementation used in FIGS. 12 and 13. In particular, FIG. 14 shows a storyboard-style illustration 1400 including a first frame 1402 sequentially before a second frame 1404, according to an exemplary embodiment. The first frame 1402 corresponds to occurrence of an interruption and deviation from the haptic plane 1207, and the second frame 1304 corresponds to the result of successful recovery alignment to the haptic plane.

In the example of illustration 1400, the interruption and deviation occurs with the surgical tool greater than the threshold distance from the femur 206 or planned resection volume 1206. That is, as shown in the first frame 1402, the surgical tool 234 is positioned outside the demarcation line 1214 (i.e., such that the demarcation line 1214 is between the surgical tool 234 and the femur 206). Accordingly, with reference back to FIG. 10, the process 1000 will proceed to step 1010 wherein the surgical tool is moved to a position a first distance from the femur 206, i.e., to different distance than in the examples of FIGS. 12 and 13. In particular, the second frame 1404 shows that the recovery alignment moves the surgical tool to a normal landing line 1406 in this scenario. The normal landing line 1406 is positioned further from planned resection volume 1206 than the close-in landing line, and may correspond to a position to which the surgical tool is aligned at the initiation of bone preparation. Accordingly, when the surgical tool is sufficiently offset from the planned resection volume and/or the haptic planned after the interruption, as in the example of illustration 1400, the surgical system 200 can provide recovery alignment that resets the surgical tool 234 to a position where bone preparation was initiated.

As shown in the second frame 1404, the angular orientation of the surgical tool 234 has been adjusted to be perpendicular to the normal landing line 1406. Thus, in the example of illustration 1400, the surgical tool is rotated in the haptic plane 1207 between the first frame 1402 and the second frame 1404. This is consistent with some implementations of the process 600 of FIG. 6, in particular an example where the surgical tool 234 is aligned to a predetermined pose if the first pose of surgical tool 234 from the first frame 1402 is outside the threshold distance from the femur 206. FIG. 14 thus illustrates one of multiple ways in which the various systems and methods described herein can be used together and adapted to combine to provide various advantageous features for users of robotically-assisted surgical systems.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, magnetic, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed is:

1. A method of operation of a robotically-assisted surgical system, comprising:
   defining a virtual geometry associated with a planned resection;
   determining a first pose of a surgical tool in response to an interruption of performance of the planned resection;
   intraoperatively defining a target orientation for the surgical tool on using the first pose such that the target orientation corresponds to an angle of the surgical tool in the virtual geometry at the interruption;
   controlling a robotic device to automatically move the surgical tool to both the virtual geometry and the target orientation.

2. The method of claim 1, wherein determining the first pose of the surgical tool comprises:
   detecting the interruption of performance of the planned resection; and
   determining the first pose the surgical tool in the virtual geometry in response to detecting the interruption using data from an optical tracking system.

3. The method of claim 2, wherein controlling the robotic device to automatically move the surgical tool into both the virtual geometry and the target orientation causes return of the surgical tool to the angle of the surgical tool in the virtual geometry at the interruption.

4. The method of claim 1, wherein determining the first pose of the surgical tool comprises:
   detecting a user request to initiate automated alignment of the surgical tool to the virtual geometry;
   initiating the controlling the robotic device when the user request is detected.

5. The method of claim 1, wherein defining the target orientation for the surgical tool based on the first pose, comprises:
   determining whether the first pose is in a first category or a second category;
   defining the target orientation as a first orientation if the first pose is in the first category and defining the target orientation as a second orientation if the first pose is in the second category.

6. The method of claim 5, wherein:
   the first category corresponds to poses in which the surgical tool points at least partially in a medial-to-lateral direction with respect to a joint of a patient; and
   the second category corresponds to poses in which the surgical tool points at least partially in a lateral-to-medial direction with respect to the joint of the patient.

7. The method of claim 5, wherein:
   the first orientation is dynamically defined to comprise an angle of the first pose; and
   the second orientation is static and predefined.

8. The method of claim 7, wherein the second orientation is perpendicular to a medial-to-lateral direction with respect to the joint of a patient.

9. The method of claim 1, wherein controlling the robotic device to automatically move the surgical tool to both the virtual geometry and the target orientation comprises causing the robotic device to automatically move for a duration greater than a preset lower bound on the duration and less than a preset upper bound on the duration.

10. A surgical system comprising:
    a robotic device;
    a surgical tool coupled to the robotic device;
    a controller configured to:
      define a plane for performing a cut of a bone;
      control the robotic device to allow manual movement of the surgical tool in the plane while the surgical tool is used to perform the cut of the bone;
      detect an interruption of performance of the cut;
      determine a last angular orientation of the surgical tool in the plane before occurrence of the interruption; and
      control the robotic device to automatically realign the surgical tool to both the plane and the last angular orientation of the surgical tool.

11. The surgical system of claim 10, wherein the interruption is caused by a deviation from the plane, and wherein the controller is configured to:
    determine whether the deviation exceeds a threshold;
    in response to determining that the deviation exceeds the threshold, control the robotic device to move the surgical tool to a first distance from the bone while automatically realigning the surgical tool to both the plane and the last angular orientation of the surgical tool;

in response to determining that the deviation does not exceed the threshold, control the robotic device to move the surgical tool to a second distance from the bone while automatically realigning the surgical tool to both the plane and the last angular orientation of the surgical tool.

12. The surgical system of claim 11, wherein the second distance is less than the first distance.

13. The surgical system of claim 10, wherein the interruption comprises an occlusion of a tracking system.

14. The surgical system of claim 10, wherein the interruption comprises a deviation of the surgical tool from the plane.

15. Non-transitory computer-readable media storing program instructions that, when executed by one or more processors, cause the one or more processors to perform operations comprising:
    defining a virtual geometry relative to an anatomical feature;
    controlling a robotic device coupled to a tool to guide the tool with the virtual geometry;
    detecting a deviation of the tool from the virtual geometry;
    controlling the robotic device to automatically move the tool to a first position having a first distance from the anatomical feature if the deviation exceeds a threshold; and
    controlling the robotic device to automatically move the tool to a second position having a second distance from the anatomical feature if the deviation is less than the threshold.

16. The non-transitory computer-readable media of claim 15, wherein the second distance is less than the first distance.

17. The non-transitory computer-readable media of claim 15, wherein the first position and the second position are aligned with the virtual geometry.

18. The non-transitory computer-readable media of claim 15, the operations further comprising determining a last angular orientation of the tool in the virtual geometry before occurrence of the deviation;
    wherein controlling the robotic device to automatically move the tool to the second position further comprises automatically aligning the tool to the last angular orientation of the tool.

19. The non-transitory computer-readable media of claim 18, wherein controlling the robotic device to automatically move the tool to the first position further comprises automatically aligning the tool to the last angular orientation of the tool.

* * * * *